(12) United States Patent
Mathey et al.

(10) Patent No.: US 6,521,795 B2
(45) Date of Patent: Feb. 18, 2003

(54) 6,6'-BIS-(1-PHOSPHANORBORNADIENE) DIPHOSPHINES, THEIR PREPARATION AND THEIR USES

(75) Inventors: Francois Mathey, Paris (FR); Francois Mercier, Versailles (FR); Michel Spagnol, Lyons (FR); Frederic Robin, Montrouge (FR); Virginie Mouries, Paris (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/871,689

(22) Filed: Jun. 4, 2001

(65) Prior Publication Data

US 2002/0042540 A1 Apr. 11, 2002

Related U.S. Application Data

(62) Division of application No. 09/367,552, filed as application No. PCT/FR98/00424 on Mar. 4, 1998, now Pat. No. 6,288,279.

(30) Foreign Application Priority Data

Mar. 4, 1997 (FR) ............................. 97 02524

(51) Int. Cl.$^7$ ................................. C07F 9/53
(52) U.S. Cl. ........................... 568/12; 568/14
(58) Field of Search .............. 568/12, 13, 14

(56) References Cited

U.S. PATENT DOCUMENTS 5,783,738 A 7/1998 Mathey et al.

FOREIGN PATENT DOCUMENTS

WO 96 20202 7/1996

OTHER PUBLICATIONS

CA:117:48704 abs of Bull Soc Chim Fr by Bevierre et al 129(1) pp 1–8 1992.*
A. Gavezotti, J. Am. Chem. Soc., 105, 5220 (1983).
M.L. Connolly, J. Am. Chem. Soc., 107, 1118 (1985).
Journal of the American Chemical Society 95, p. 3080–3081 (1973).
J. Org. Chem. 36, p. 3520 et seq. (1971).
M. Yamagusi et al, Tetrahedron Letters, 31, p. 5049 (1990).
A.C. Cope, Journal of the American Chemical Society 90, pp. 909 (1968).
M. Mayashi et al, Tetrahedron Letters 27, p. 191 (1986).
Schrock R. and Osborn J.A., Journal of the American Chemical Society, 93, pp. 2397 (1971).
Sei Otsuka et al, Journal of the American Chemical Society 93, p. 4301 (1971).
CA:127:331575 abs of Chem Eur. J by Frederic et al 3(8) pp. 1365–1369.
CA:125:195986 abs of WO 9620202.
CA:117:48704 abs of Bull. Soc. Chim. Fr. by Bevierre et al129(1), pp. 1–8.
Ca:121:57572 as of Bull. Soc. Chime. Fr. by Laporte et al 130(6) pp. 843–850.

* cited by examiner

*Primary Examiner*—Jean F. Vollano
(74) *Attorney, Agent, or Firm*—Burns, Doane, Swecker & Mathis, L.L.P.

(57) ABSTRACT

A subject of the present invention is new 6,6'-bis-(1-phosphanorbornadiene) diphosphines, their preparation process and their use in asymmetrical catalysis.

The new diphosphines correspond to general formula (I):

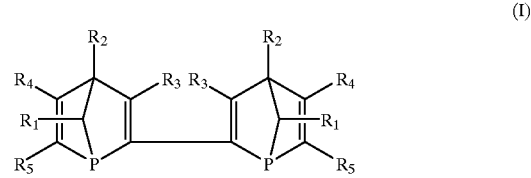

(I)

in which $R_1$, $R_2$, $R_3$, $R_4$, $R_5$ are as defined in claim 1.

18 Claims, No Drawings

6,6'-BIS-(1-PHOSPHANORBORNADIENE) DIPHOSPHINES, THEIR PREPARATION AND THEIR USES

This application is a divisional of U.S. application Ser. No. 09/367,552, filed on Jan. 13, 2000, now U.S. Pat. No. 6,288,279,which was a national stage filing under 35 U.S.C. § 371 of International Application No. PCT/FR98/00424 filed on Mar. 4, 1998, which International Application was not published by the International Bureau in English on Sep. 11, 1998.

A subject of the present invention is new 6,6'-bis-(1-phosphanorbornadiene) diphosphines and their preparation process.

Another subject of the invention is said optically active disphosphines.

Finally, other subjects are the uses of these diphosphines, in particular in asymmetrical synthesis in organic chemistry.

In numerous fields, in particular pharmaceutical, agrochemical or perfumery fields, a growing demand has been noted for optically active products which must have a useful property.

During synthesis of such products, the simultaneous production of an inactive enantiomer is generally observed which, by its presence, risks rendering a process uncompetitive from an industrial point of view.

Moreover, in certain fields (for example, pharmacology and agrochemistry), optically pure products are increasingly sought after, in order to avoid toxicity problems linked to the presence of the inactive enantiomer.

It is therefore important to minimize the formation of the enantiomer, which is not useful.

One of the means of achieving this is to conduct the reaction in the presence of asymmetrical synthesis catalysts, which can be complexes of transition metals with chiral ligands.

The problem which arises is that there are no universal chiral ligands which are suitable for conducting all chemical reactions and, given the difficulty of obtaining the correct enantiomer with a high enantiomeric excess, it is important to have all sorts of chiral ligands available in order to assess their performances.

Thus, in the Application PCT/FR95/01716, new optically active 6,6'-bis-(1-phospha-2,3-diphenyl-4,5-dimethylnorbornadiene) diphosphines were described, corresponding to the following formulae:

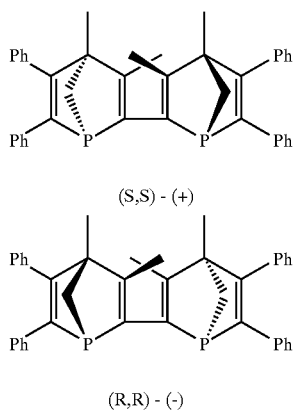

(S,S) - (+)

(R,R) - (-)

While this ligand allows useful hydrogenation catalysts to be obtained for hydrogenating certain a,b-unsaturated acids such as a-acetamidocinnamic acid, the enantiomeric excess obtained is not satisfactory in all asymmetrical catalysis reactions.

It is therefore desirable to have other chiral ligands available which can be suitable if known ligands are insufficiently enantioselective.

The difficulty is that chiral ligands of diphosphine type are not easily accessible owing to their complex synthesis and also to the difficulty in separating diastereoisomers and/or enantiomers.

A first objective of the invention is to provide new diphosphines and a process for their preparation.

Another objective is to provide optically active diphosphines, chiral as regards phosphorus and non-racemizable.

Another objective is to provide modified diphosphines allowing better results to be obtained in asymmetrical catalysis reactions.

New products have now been found constituting the first subject of the invention, namely 6,6'-bis-(1-phosphanorbornadiene) diphosphines corresponding to the following formula:

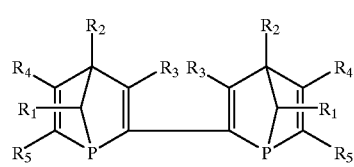

(I)

in said formula (I):
$R_1$, $R_2$, $R_3$, $R_4$, $R_5$, identical or different, represent a hydrogen atom or hydrocarbon radical, optionally substituted, having from 1 to 40 carbon atoms, which can be a linear or branched, saturated or unsaturated acyclic aliphatic radical; a monocyclic or polycyclic, saturated, unsaturated or aromatic, carbocyclic or heterocyclic radical; a linear or branched, saturated or unsaturated aliphatic radical, carrying a cyclic substituent, $R_2$ and $R_3$ together with the carbon atoms which carry them can form a saturated or unsaturated ring, $R_5$ can represent a radical of

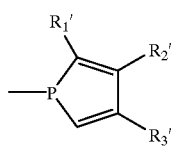

type, in which $R_1'$, $R_2'$ and $R_3'$ have the same meaning as that given for $R_1$, $R_2$ and $R_3$, $R_4$ and $R_5$ cannot simultaneously represent a phenyl group.

In general formula (I), $R_1$, $R_2$, $R_3$, $R_4$, $R_5$, identical or different, can assume various meanings. Different examples are given hereafter but are in no way limitative.

Thus $R_1$ to $R_5$ can represent a linear or branched, saturated or unsaturated, acyclic aliphatic radical.

More precisely, $R_1$ to $R_5$ represent a linear or branched acyclic aliphatic radical preferably having 1 to 12 carbon atoms, saturated or comprising one to several, generally 1 to 3, double bonds.

The hydrocarbon chain can optionally be interrupted by a group, preferably a heteroatom, and more particularly an oxygen or nitrogen atom or can carry substituents, for example a halogen atom, in particular chlorine or a —$CF_3$ group.

It is also possible that in the diphosphine of formula (I), $R_1$ to $R_5$ represent a linear or branched, saturated or unsaturated acyclic aliphatic radical which can optionally carry a cyclic substituent. By ring is understood a saturated, unsaturated or aromatic, carbocyclic or heterocyclic ring.

As examples of cyclic substituents, aromatic or heterocyclic cycloaliphatic substituents can be envisaged, in particular cycloaliphatic substituents comprising 6 carbon atoms in the ring or benzene substituents, these cyclic substituents themselves optionally carrying one or more substituents.

As examples of such radicals there can be mentioned amongst others the benzyl radical.

In general formula (I) for diphosphines, the $R_1$ to $R_5$ radicals can also represent a carbocyclic radical, saturated or comprising 1 or 2 unsaturations in the ring, generally having 3 to 8 carbon atoms, preferably 6 carbon atoms in the ring; said ring being able to be substituted.

As preferred examples of $R_1$ to $R_5$ radicals, there can be mentioned the cyclohexyl radicals optionally substituted by linear or branched alkyl radicals having 1 to 4 carbon atoms.

$R_1$ to $R_5$ can be saturated or unsaturated polycyclic carbocyclic radicals, preferably bicyclic, which means that at least two rings have two carbon atoms in common. In the case of the polycyclic compounds, the number of carbon atoms in each ring preferably varies from 3 to 6: the total number of carbon atoms preferably being equal to 7.

Thus, the $R_1$ to $R_5$ radicals preferentially represent an aromatic hydrocarbon radical, and in particular a benzene radical corresponding to general formula (II):

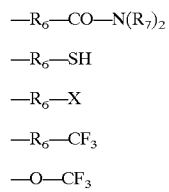

(II)

in said formula (II):
  n is an integer from 0 to 5, preferably from 0 to 3,
  Q represents $R_0$, one of the following groups or functions:
    a linear or branched alkyl radical having from 1 to 6 carbon atoms, preferably from 1 to 4 carbon atoms, such as methyl, ethyl, propyl, isopropyl, butyl, isobutyl, sec-butyl, tert-butyl,
    a linear or branched alkenyl radical having from 2 to 6 carbon atoms, preferably from 2 to 4 carbon atoms, such as vinyl, allyl,
    a linear or branched alkoxy radical having from 1 to 6 carbon atoms, preferably from 1 to 4 carbon atoms such as the methoxy, ethoxy, propoxy, isopropoxy, butoxy radicals,
    an acyl group having from 2 to 6 carbon atoms,
    a radical of formula:

—$R_6$—OH
      —$R_4$—COO$R_7$
      —$R_6$—CHO
      —$R_6$—NO$_2$
      —$R_6$—CN
      —$R_6$—N($R_7$)$_2$
      —$R_6$—CO—N($R_7$)$_2$
      —$R_6$—SH
      —$R_6$—X
      —$R_6$—CF$_3$
      —O—CF$_3$ in said formulae, $R_6$ represents a valency bond or a saturated or unsaturated, linear or branched, divalent hydrocarbon radical having from 1 to 6 carbon atoms such as, for example, methylene, ethylene, propylene, isopropylene, isopropylidene; the $R_7$ radicals, identical or different, represent a hydrogen atom or a linear or branched alkyl radical having from 1 to 6 carbon atoms; X symbolizes a halogen atom, preferably a chlorine, bromine or fluorine atom.

Q represents $R_0'$, one of the following more complex radicals:

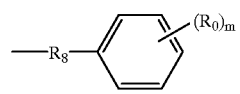

in which:
  m is an integer from 0 to 5, preferably from 0 to 3,
  $R_0$ has the meaning indicated previously,
  $R_8$ represents a valency bond; a saturated or unsaturated, linear or branched divalent hydrocarbon group having from 1 to 6 carbon atoms such as for example methylene, ethylene, propylene, isopropylene, isopropylidene or one of the following groups called Z: —O—; —CO—; COO—; —N$R_7$—; —CO—N$R_7$—; —S—; —SO$_2$—; —N$R_7$—CO—;
  in said formulae, $R_7$ represents a hydrogen atom, a linear or branched alkyl group having from 1 to 6 carbon atoms, preferably a methyl or ethyl radical.

When n is greater than 1, the Q radicals can be identical or different and 2 successive carbon atoms of the benzene ring can be joined together by a ketal bridge such as the extranuclear methylene dioxy or ethylene dioxy radicals.

Among all the aforementioned $R_1$ to $R_5$ radicals, the preferred diphosphines correspond to general formula (I) in which $R_1$ to $R_5$ represent an aromatic radical corresponding to general formula (II) in which:
  n is equal to 0, 1, 2 or 3,
  Q represents one of the following groups or functions:
    a hydrogen atom
    a linear or branched alkyl radical, having from 1 to 4 carbon atoms,
    a linear or branched alkoxy radical having from 1 to 4 carbon atoms,
    a benzoyl group,
    an —OH group,
    a —CHO group,
    an NH$_2$ group,
    an NO$_2$ group,
    a phenyl radical,
    a halogen atom,
    a CF$_3$ group.

Even more preferentially, the compounds of formula (I) are chosen in which the identical or different Q radicals are a hydrogen atom, an alkyl radical having from 1 to 4 carbon atoms.

As examples of radicals $R_1$ to $R_5$ corresponding to formula (I), there can be mentioned more specifically the phenyl, tolyl or xylyl, 1-methoxyphenyl, 2-nitrophenyl radicals, and the biphenyl, 1,1'-methylenebiphenyl, 1,1'-isopropylidenebiphenyl, 1,1'-carboxybiphenyl, 1,1'-oxybiphenyl, 1,1'-iminobiphenyl radicals: said radicals being able to be substituted by one or more substituents.

$R_1$ to $R_5$ can also represent a polycyclic aromatic hydrocarbon radical; the rings being able to form together ortho-condensed, ortho- and peri-condensed systems. There can more particularly be mentioned a naphthyl radical; said rings being able to be substituted.

In general formula (I) for diphosphines, $R_1$ to $R_5$ can also represent a saturated, unsaturated or aromatic heterocyclic radical, in particular comprising 5 or 6 atoms in the ring including 1 or 2 heteroatoms such as the nitrogen, sulphur and oxygen atoms; the carbon atoms of the heterocycle being optionally substituted.

$R_1$ to $R_5$ can also represent a polycyclic heterocyclic radical defined as being either a radical constituted by at least 2 aromatic heterocycles or heterocycles not containing at least one heteroatom in each ring and forming together ortho- or ortho- and peri-condensed systems or a radical constituted by at least one aromatic or non-aromatic hydrocarbon ring and at least one aromatic or non-aromatic heterocycle together forming ortho- or ortho- and peri-condensed systems; the carbon atoms of said rings being optionally substituted.

As examples of $R_1$ to $R_5$ groups of heterocyclic type, there can be mentioned among others the furyl, pyrrolyl, thienyl, isoxazolyl, furazannyl, isothiazolyl, imidazolyl, pyrazolyl, pyridyl, pyridazinyl, pyrimidinyl, pyrannyl radicals and the quinolyl, naphthyridinyl, benzopyrannyl, benzofurannyl, indolyl radicals.

In the case where $R_5$ represents a radical of

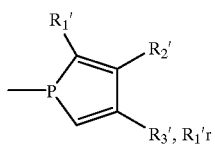

type, $R_1'$ preferably represents a hydrogen atom and $R_2'$ and $R_3'$ preferably represent a methyl radical.

It should be noted that if one of the $R_1$ to $R_5$ radicals comprises any one ring, it is possible for this ring to carry a substituent.

The number of substituents present on the ring depends on the carbon condensation of the ring and the presence or absence of unsaturations on the ring. The maximum number of substituents which can be carried by a ring is easily determined by a person skilled in the art.

The substituent can be of any type provided that it does not interfere at the level of the desired product. $R_0$ illustrates the type of substituents commonly encountered. The substituents carried most often by the ring are one or more alkyl or alkoxy radicals preferably having 1 to 4 carbon atoms and/or a halogen atom.

In the case where the $R_1$ to $R_5$ radicals comprise an unsaturation such as a double bond, it is preferable for one of the carbon atoms of the double bond to be a disubstituted carbon, i.e. carrying two substituents and there can in particular be mentioned the alkyl radicals preferably having 1 to 4 carbon atoms.

As regards the $R_2$ and $R_3$ radicals, they can together with the carbon atoms which carry them form a saturated or unsaturated ring preferably having from 5 to 7 carbon atoms and more preferentially 6 carbon atoms. It can be mentioned, among other things, that the $R_2$ and $R_3$ radicals can form a cyclohexane.

Among the diphosphines corresponding to formula (I), the different radicals represent more particularly:

for the $R_1$ and $R_2$ radicals,
a hydrogen atom,
a linear or branched alkyl radical having from 1 to 4 carbon atoms, for the $R_3$ radical,
a radical other than a hydrogen atom, preferably a linear or branched alkyl radical having from 1 to 4 carbon atoms, a phenyl radical, and for the $R_4$ and $R_5$ radicals,
a hydrogen atom,
a linear or branched alkyl radical having from 1 to 4 carbon atoms,
a phenyl radical or a phenyl radical carrying one or more substituents, preferably 1 to 3 linear or branched alkyl or alkoxy radicals having 1 to 4 carbon atoms, a naphthyl radical, $R_4$ and $R_5$ cannot simultaneously represent a phenyl group.

In its preferred form, the invention relates to new diphosphines corresponding to formula (I') in which the $R_5$ radical can represent a sterically hindered group such as a substituted phenyl radical or a tertiary radical, i.e. the carbon atom located in b position with respect to the phosphorus atom carries three substituents (for example a tert-butyl radical).

By sterically hindered group is understood a group having a sterical hindrance greater than that of a phenyl radical and which can be determined by the molecular volume.

For the determination of the molecular volume, reference can be made to the data in the literature and in particular to the articles A. Gavezotti, J. Am. Chem. Soc., 105, 5220 (1983) and M. L. Connolly, J. Am. Chem. Soc., 107, 1118 (1985).

Thus, the diphosphines corresponding more particularly to the following formula (I') show specific characteristics:

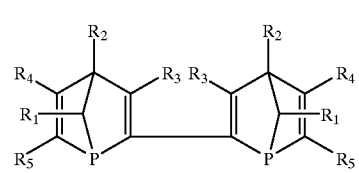

(I')

in said formula (I'):
$R_1, R_2, R_3, R_4$, identical or different, represent a hydrogen atom or a hydrocarbon radical, optionally substituted, having from 1 to 40 carbon atoms, which can be a saturated or unsaturated, linear or branched acyclic aliphatic radical; a saturated, unsaturated or aromatic, monocyclic or polycyclic, carbocyclic or heterocyclic radical; a saturated or unsaturated, linear or branched aliphatic radical carrying a cyclic substituent, $R_2$ and $R_3$ can form together with the carbon atoms which carry them a saturated or unsaturated ring, $R_5$ represents a saturated or unsaturated branched aliphatic radical the characteristic of which is having a tertiary radical located in b position with respect to the phosphorus atom and there can in particular be mentioned a tert-butyl radical; a phenyl radical carrying at least one substituent, preferably one or more alkyl or alkoxy radicals having from 1 to 4 carbon atoms or a naphthyl radical, $R_4$ and $R_5$ cannot simultaneously represent a phenyl group.

Diphosphines of Formula (I)

Another subject of the invention relates to the preparation process for diphosphines of formula (I) characterized in that it consists in reacting:

a diphosphole of formula (III) originating from the rearrangement of the diphosphole of formula (IV):

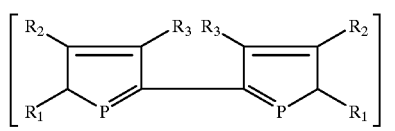

(III)

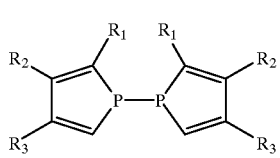

(IV)

in said formulae (III) and (IV), $R_1$, $R_2$ and $R_3$ have the meaning indicated previously, and an acetylenic compound of formula (V):

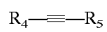  (V)

in said formula (V), $R_4$ and $R_5$ have the meaning given previously.

The diphosphines of formula (I) are therefore obtained by reaction between a diphosphole of formula (III) and an acetylenic compound of formula (V).

The diphospholes of formula (III) are prepared from diphospholes of formula (IV) according to a rearrangement obtained by thermal treatment carried out at a temperature comprised between 100° C. and 200° C., preferably between 130° C. and 150° C.

As diphospholes of formula (IV) preferentially implemented, there can be mentioned:

1,1'-bis-(3,4-dimethylphosphole),
1,1'-bis-(3-methylphosphole),
1,1'-bis-(phosphole).

As regards the acetylenic compound of formula (V), use is preferentially made of:

acetylene,
methylacetylene,
tert-butylacetylene,
phenylacetylene,
phenylmethylacetylene,
o-tolylacetylene,
bis-(o-tolylacetylene),
phenyl-tert-butylacetylene,
phenylmesitylacetylene,
bis-(mesityl)acetylene.

The acetylenic compounds of formula (V) are products which can be obtained according to the processes described in the literature [in particular Journal of the American Chemical Society 95, p. 3080–3081 (1973) and J. Org. Chem. 36, p. 3520 et seq. (1971)].

The quantity of acetylenic compound of formula (V) expressed in moles of acetylenic compound per mole of diphosphole of formula (IV) can also vary within wide limits. The acetylenic compound of formula (V)/diphosphole of formula (IV) molar ratio can vary between 1 and 4, preferably between 1 and 1.5.

The reaction is advantageously carried out without a solvent. However, it is desirable to use an organic solvent, preferably apolar, aprotic when one wishes to solubilize the acetylenic compound.

As examples of solvents suitable for the present invention, there can in particular be mentioned the aliphatic, cycloaliphatic or aromatic hydrocarbons.

As examples of aliphatic or cycloaliphatic hydrocarbons, there can be mentioned more particularly paraffins such as in particular hexane, heptane, octane, nonane, decane, undecane, dodecane, tetradecane, cyclohexane, aromatic hydrocarbons such as in particular benzene, toluene, xylenes, cumene, petroleum cuts constituted by a mixture of alkylbenzenes, in particular cuts of Solvesso® type.

The preferred solvents are toluene and xylenes.

A mixture of organic solvents can also be used.

The highest possible concentration of diphosphole in the medium is selected. It is most often comprised between 1 and 25 mol per liter of medium and, preferably, between 5 and 10 mol per liter.

The reaction temperature is as stated previously, between 100° C. and 200° C., preferably between 130° C. and 150° C.

Generally, the reaction is carried out under atmospheric pressure, but higher pressures can also be suitable, ranging from 1 to 50 bar, preferably from 1 to 25 bar. The process is carried out under autogenous pressure when the reaction temperature is greater than the boiling point of the reagents and/or the products.

It is preferred to carry out the reaction under a controlled atmosphere of inert gases such as nitrogen or the rare gases, for example argon.

The duration of the reaction can be very variable. It is most frequently between 15 minutes and 10 hours, preferably between 30 minutes and 5 hours.

From a practical point of view, the process can be implemented discontinuously or continuously.

A practical implementation consists of loading the diphosphole of formula (IV), the acetylenic compound of formula (V) preferably diluted in the organic solvent. The inert gas atmosphere is established followed by heating under a closed atmosphere.

At the end of the reaction, a mixture of two diastereoisomers is obtained, a diphosphine in meso form (I m) and a diphosphine in racemic form (Ir):

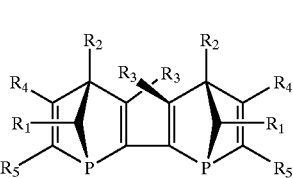

(Im)

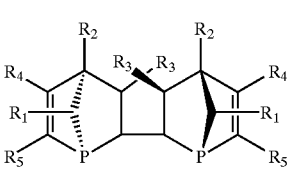

(Ir)  +

-continued

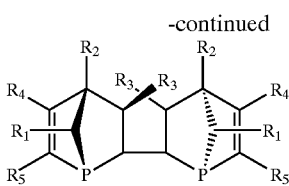

in the formulae (Im) and (Ir), the different symbols have the meaning given previously.

Diphospholes of Formula (IV)

A method of accessing the compounds of formula (IV) used as starting reagents for the preparation of the diphosphines relates to a process which consists in reacting:

a compound of formula (VI):

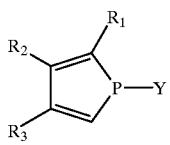

(VI)

in formula (VI), $R_1$, $R_2$, $R_3$ have the meanings indicated previously, and Y represents any group, preferably an aromatic carbocyclic radical, and more preferentially, a phenyl radical or an aromatic heterocyclic radical, with an alkali metal, leading to a compound of formula (VII):

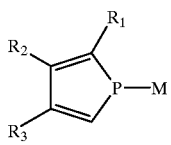

(VII)

in formula (VII), $R_1$, $R_2$, $R_3$ have the meanings indicated previously, and M represents an alkali metal, preferably lithium or sodium.

dimerizing the compound of formula (VII) into a compound of formula (IV).

The phosphole of formula (VI) is reacted with an alkali metal which can be sodium or any other alkali metal, but more preferentially lithium.

The metal is generally in excess. Thus the ratio between the number of gram-atoms of alkali metal and the number of moles of compound of formula (VI) advantageously varies between 2 and 3.

The compound of formula (VI) and the alkali metal are reacted at a temperature comprised between 10° C. and 40° C., preferably between 10° C. and 20° C.

The reaction generally lasts between 30 minutes and 2 hours.

The reaction is advantegously carried out in an organic solvent, preferably an aprotic polar solvent. There can in particular be mentioned aliphatic, cycloaliphatic or aromatic ether oxides and, more particularly, diethyl oxide, dipropyl oxide, diisopropyl oxide, dibutyl oxide, methyltertiobutylether, dipentyl oxide, diisopentyl oxide, ethyleneglycol dimethylether (or 1,2-dimethoxyethane), diethyleneglycol dimethylether (or 1,5-dimethoxy 3-oxapentane); benzyl oxide; dioxane, tetrahydrofuran (THF).

Among said solvents, tetrahydrofuran is preferentially used.

The quantity of organic solvent used can vary very widely. The ratio between the number of moles of solvent and the number of moles of substrate can thus range from 10 to 40 and is preferably comprised between 20 and 25.

A preferred variant consists of trapping the YM compound which has formed. For this purpose, a Lewis acid is used, preferably $AlCl_3$ and optionally a tertiary alkyl halide, preferably tert-butyl chloride.

Said reagents are used in an equal quantity or a quantity close to the stoichiometric quantity.

From a practical point of view, there are no constraints to be observed. The phosphole of formula (VI) can be loaded, with excess alkali metal.

The reaction is left to run for 30 minutes to 2 hours.

The excess metal is eliminated (solid/liquid separation), then Lewis acid and/or tertiary alkyl halide is added, between 0° C. and 20° C.

In the following stage, the compound of formula (VII) is dimerized.

The iodine is preferentially used as coupling agent, preferably used in a stoichiometric quantity.

The reaction is generally carried out in the same type of organic solvent as in the previous stage.

The reaction is carried out at ambient temperature (generally between 15° C. and 25° C.).

The diphosphole of formula (IV) is obtained.

Phospholes of Formula (VI)

The compound of formula (VI) can be obtained by reacting a diene of formula (VIII) with a dihalogenarylphosphine:

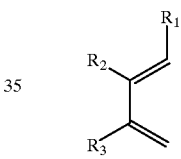

(VIII)

in formula (VIII), $R_1$, $R_2$, $R_3$ have the meanings given previously.

As examples of dihalogenarylphosphines used, use is generally made of dichlorophenylphosphine, dibromophenylphosphine or their mixtures preferably comprising equimolar quantities of each of the dihalogenphosphines.

The compound of formula (VIII) and dihalogenarylphosphine are mixed, used in stoichiometric or similar quantities.

According to a practical implementation, the dienic compound of formula (VIII) is reacted with dihalogenarylphosphine, generally solubilized in an appropriate solvent, preferably an aliphatic or aromatic halogenated hydrocarbon.

There can more particularly be mentioned dichloromethane, 1,2-dichloroethane; monochlorobenzene, 1,2-dichlorobenzene, 1,3-dichlorobenzene, 1,4-dichlorobenzene, 1,2,4-trichlorobenzene or mixtures of different chlorobenzenes; monobromobenzene or mixtures of monobromobenzene with one or more dibromobenzenes; 1-bromonaphthalene.

Dichloromethane is more preferentially chosen.

The concentration of dihalogenarylphosphine in the medium can vary within wide limits. It can thus be comprised between 5 and 20 mol per liter of medium and, preferably, is approximately 10 mol per liter.

The reaction is advantageously carried out between 0° C. and 20° C., preferably sheltered from the air. It lasts from one to several days, for example 15 days.

At the end of the reaction, a phospholenium salt is obtained ($P^+X^-$).

The phosphole of formula (VI) results from the elimination of 2 moles of HX per mole of dihalogenarylphosphine, which is carried out in the presence of an amine, preferably a tertiary amine.

As more specific examples, there can be mentioned picolines, pyridine, 2-ethylpyridine, 4-ethylpyridine, 2-methylpyridine, 4-methylpyridine, 2,6-dimethylpyridine, imidazole, 1-methylimidazole, TMEDA (tetramethylenediamine), N-methylpyrrolidine, 4-methylmorpholine, triethylamine, DBU (1,8-diazabicyclo [5.4;0.]undecene-7).

The quantity of amine is generally equal to twice the stoichiometric quantity of dihalogenarylphosphine, i.e. 2 or 3 times in excess of the stoichiometry.

The reaction is advantageously carried out in a mixture of two organic solvents, one solubilizing the phosphole obtained, the other solubilizing the amine salts formed in order to facilitate subsequent separation.

As examples of solvents suitable for extracting the phosphole obtained, there can be mentioned in particular the aliphatic, cycloaliphatic or aromatic hydrocarbons. For examples, reference can be made to the list given previously.

As regards the solubilization of the amine salts obtained, use can be made of, among others, aliphatic or aromatic halogenated hydrocarbons, as previously mentioned.

The preferred pair of solvents is hexane and dichloromethane preferably used in similar or equal volumes.

The concentration of diphosphole in the medium can vary within wide limits. It can thus be comprised between 1 and 5 mol per liter of medium and, preferably between 2 and 3 mol per liter.

A mixture of organic solvents as indicated above and a base, preferably an amine, are then introduced.

At the end of the reaction, if necessary, the excess amine is neutralized with an acid solution, preferably a mineral acid solution, such as for example hydrochloric acid.

The organic phases are then separated.

It is possible to subject the organic phase containing the amine salts to a standard treatment in order to recover the phosphole it may contain.

The treatment consists of extraction with a solvent of the phosphole, washing the organic phase, generally with water and frequently followed by standard drying over a desiccant, for example sodium or magnesium sulphate.

The organic phases containing the phosphole are combined, then, after evaporation of the solvent, a phosphole of formula (VI) is recovered.

Diphosphine Dioxides in Meso or Racemic Form

Another subject of the invention relates to diphosphine dioxides in meso and racemic form as well as the process for obtaining them.

In fact, according to what is described in the state of the art, it is impossible in the context of the preparation of all the diphosphines of formula (I) to separate the two diastereoisomers by forming a palladium chelate (II).

It has thus been found that the diastereoisomers could be separated according to a process which consists in subjecting the mixture of diastereoisomers to an oxidization reaction thus converting them into diphosphine dioxides, then separating the diphosphine dioxides into the two diastereoisomers.

According to a first operation, the diastereoisomers are converted into oxide form.

They can be symbolized by the following formula:

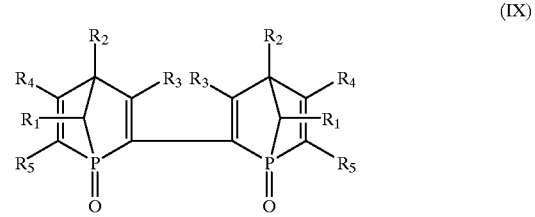

in formula (IX), the different symbols have the meaning given previously.

The diphosphine oxides of formula (IX) are obtained by oxidizing the two diastereoisomers of formula (Im) and (Ir) using an oxidizing agent.

Although it is possible to use any type of oxidizing agent, a chemical oxidant, for example potassium permanganate or molecular oxygen or a gas containing same, it is preferable to use hydrogen peroxide, preferably in the form of an aqueous solution.

The concentration of the hydrogen peroxide solution is advantageously comprised between 10% and 35% by weight.

The quantity of oxidizing agent used can vary widely from the stoichiometric quantity up to an excess representing for example 20 times the stoichiometry.

Use is made of an organic solvent which solubilizes all the reagents. The solvent can be chosen from the aliphatic, cycloaliphatic or aromatic hydrocarbons, preferably aromatic. Examples are given above.

Among all these solvents, toluene and xylenes are preferred.

The concentration of the diphosphine in the reaction solvent is preferably between 0.05 and 1 mole/liter and even more particularly between 0.05 and 0.2 mole/liter.

The diastereoisomers are therefore brought into contact, generally dissolved in an appropriate solvent, in contact with the oxidizing agent.

The reaction is advantageously carried out between 50° C. and 100° C.

The duration of the reaction is generally between 30 minutes and 4 hours.

Diphosphine oxidies are recovered in the organic phase.

The aqueous and organic phases are separated.

The phases are treated in a standard manner.

The aqueous phase is thus washed several times (from 1 to 3) with an organic solvent for the extraction of diphosphine oxides, for example ethyl ether.

All the organic phases are combined and washed with salt water (saturated solution of sodium chloride) preferentially followed by standard drying operation over a desiccant, for example sodium or magnesium sulphate.

In a following stage, the oxides of the two diastereoisomers are separated.

The solvent is concentrated by evaporation, then the separation is carried out in a known manner [A. Bertheillier—Dunod Paris (1972)] by liquid column chromatography, preferably with a silica support.

The column is eluted with a mixture of appropriate solvents.

Suitable solvents for separation are determined by simple operations executed by a person skilled in the art which consist in carrying out chromatography on a silica plate.

The solvents are generally chosen from ethyl acetate, methanol, ethyl ether or their mixtures.

Thus, depending on the case, the following are recovered from the elution solvents in a variable order: diphosphine dioxide in meso form (IXm) and diphosphine dioxide in racemic form (IXr).

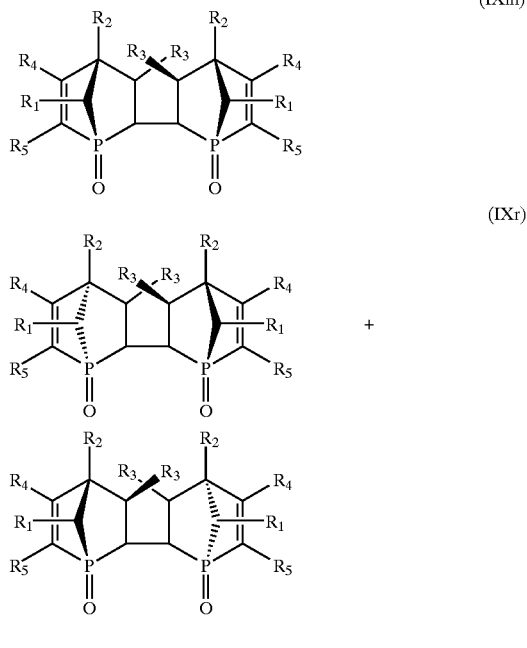

(IXm)

(IXr)

in formulae (IXm) and (IXr), the different symbols have the meanings given previously.

Diphosphine Disulphides in Racemic or Meso Form

Another subject of the invention relates to diphosphine disulphides in meso and racemic form as well as the process for obtaining them.

It has also been found that the diastereoisomers could be separated according to a process which consists in reacting the mixture of diastereoisomers (Im) and (Ir) with sulphur, thus converting them into diphosphine disulphides (IX'm) and (IX'r), then separating the two diastereoisomers of the diphosphine disulphides.

According to a first operation, the diastereoisomers are converted into sulphide form.

They can be symbolized by the following formula:

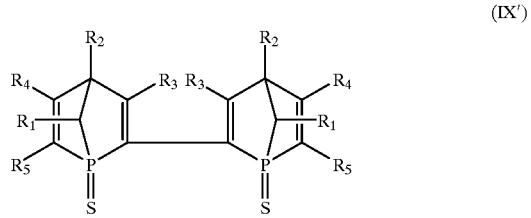

(IX')

in formula (IX'), the different symbols have the meaning given previously.

The sulphur ($S_8$) is thus reacted with the mixture of two diastereoisomers in meso form (Im) and in racemic form (Ir) leading to a mixture of diphosphine disulphides, in meso or racemic form.

The quantity of sulphur used defined with respect to each phosphorus atom generally varies from the stoichiometric quantity up to a slight excess of 10%.

The reaction takes place at a temperature ranging from ambient temperature to approximately 100° C., preferably in the region of 80° C., in a solvent preferably of aromatic hydrocarbon type, and in particular toluene.

In a following stage, the mixture of diastereoisomers is separated on a silica column as previously described.

The diphosphine disulphide is thus recovered in meso form (IX'm) and the diphosphine disulphide is recovered in racemic form (IX'r):

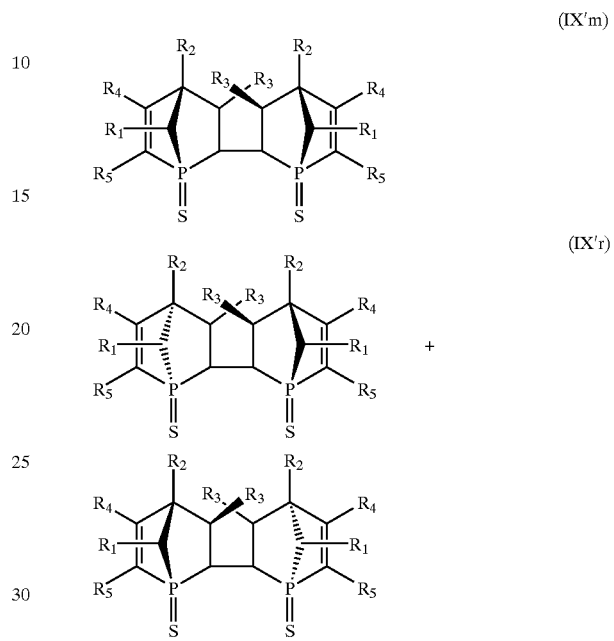

(IX'm)

(IX'r)

Diphosphines in Enantiomeric Form

Another subject of the present invention is optically active 6,6'-bis-(1-phosphanorbornadiene) diphosphines corresponding to the following formulae:

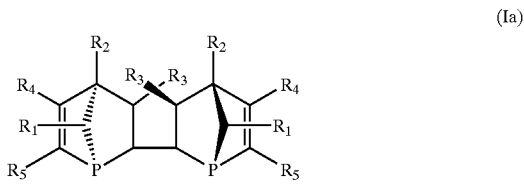

(Ia)

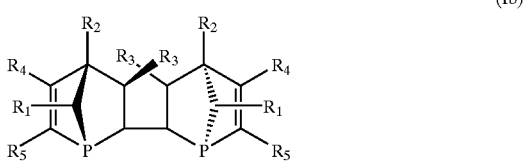

(Ib)

in formulae (Ia) and (Ib), the different symbols have the meaning given previously.

The invention therefore provides diphosphines which are chiral on phosphorus and non racemiable.

A first variant for obtaining an optically active diphosphine of formula (Ia) or (Ib) consists in resolving the diphosphine dioxide in racemic form (IXr) then separately reducing the diphosphine dioxide enantiomers obtained (IXa) or (IXb).

Another variant of the invention consists in first reducing the diphosphine dioxide in racemic form (IXr) to a diphosphine in racemic form (Ir), then resolving the diphosphine in racemic form (Ir) into enantiomers (Ia) and (Ib).

Another variant of the invention consists in resolving the racemic mixture of diphosphine disulphides (IX'r) preferably on a chiral column then reducing the diphosphine disulphide enantiomers (IX'a) an (IX'b) into diphosphine enantiomers (Ia) and (Ib).

Another variant consists in reducing the racemic mixture of diphosphine disulphides (IX'r) into the diphosphine racemic mixture (Ir) then resolving the racemic diphosphine mixture into enantiomers (Ia) and (Ib).

Another variant of the invention of the invention is to convert the racemic mixture of diphosphine disulphides (IX'r) into a racemic mixture of diphosphine dioxides (IXr) and then obtaining optically active diphosphines (Ia) and (Ib) according to the methods previously described.

According to a first implementation of the invention, the racemic mixture of diphosphine dioxides (IXr) is resolved. The resolution can be carried out by separating the two enantiomers, by chiral liquid chromatography. A chiral column is used, for example Chirosebond C1® (chiral polymer graft of starch hydrolysate type on spherical silica 5 mm-100 Å) and the elution solvents can in particular be a water/acetonitrile mixture.

In this way, two enantiomers are obtained:

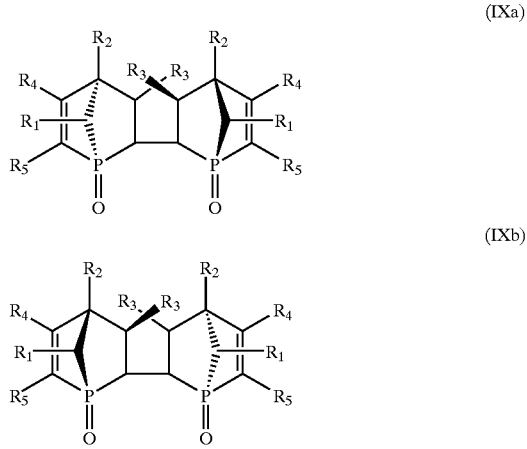

in formulae (IXa) and (IXb), the different symbols have the meaning given previously.

In a following stage, the optically active diphosphine dioxides of formula (IXa) or (IXb) are reduced. Reference can be made to the description of the reduction operation given hereafter.

Another variant first consists in reducing the diphosphine dioxide in racemic form then resolving the diphosphine in racemic form obtained.

The reduction can be carried out with a reduction agent such as for example trichlorosilane, hexachlorodisilazane, phenyltrisilane, a hydride in particular $LiAlH_4$ or $NaBH_4$.

The quantity of reducing agent used can vary widely from the stoichiometric quantity to an excess representing for example 20 times the stoichiometry.

When a reducing agent is used which leads to the release of a halogenated acid, for example trichlorosilane or hexachlorosilazane, a base is added, preferably an amine so that it traps the halogenated (hydrochloric) acid released.

As more specific examples, there can be mentioned picolines, pyridine, 2-ethylpyridine, 4-ethylpyridine, 2-methylpyridine, 4-methylpyridine, 2,6-dimethylpyridine, imidazole, 1-methylimidazole, TMEDA (tetramethylenediamine), N-methylpyrrolidine, 4-methylmorpholine, triethylamine, DBU (1,8-diazabicyclo [5.4;0.]undecene-7).

The quantity of amine is at least equal to the quantity necessary to trap the halogenated acid released and is more generally in excess, of up to 3 times the stoichiometric quantity.

The reaction is carried out in an organic solvent which solubilizes all the reagents. The solvent can be chosen from aliphatic, aromatic, halogenated or non-halogenated hydrocarbons.

Among all these solvents, toluene and dichloromethane are preferred.

The concentration of diphosphine in the reaction solvent is preferably between 0.05 and 1 mole/liter and even more particularly between 0.05 and 0.2 mole/liter.

From a practical point of view, in a mixture of solvents and in the presence of an amine, the racemic compound is generally added in the form of oxides followed by the reducing agent.

The reaction is advantageously carried out between 50° C. and 100° C.

The duration of the reaction is generally between 30 minutes and 4 hours.

The racemic mixture is in organic phase.

It is sometimes necessary to carry out basic treatment where the reducing agent is in excess in order to destroy it.

After cooling down, a base is then added, preferably soda, potash or sodium carbonate, until a basic pH is obtained (pH of at least 8). Preferably, a basic aqueous solution is used, preferably a soda solution having a concentration of 10% to 30%.

The aqueous and organic phases are separated.

The diphosphine enantiomers are recovered from the organic phase which is subjected to standard treatment as described previously, extraction with a solvent, washing with salt water and optionally drying.

A racemic mixture of the two enantiomers is obtained which can then be separated.

In this way, according to the process of the invention, there follows the separation of a meso compound (Im) and a racemic compound (Ir), which are also new products.

According to another subject of the invention, the racemic mixture of 6,6'-bis-(1-phosphanorbornadiene) is resolved according to a process which consists in reacting it with a palladium and/or platinum complex as chiral auxiliary, in an organic solvent thus forming diastereoisomeric complexes, then resolving said optically pure complexes.

In conformity with the process of the invention, use is made of a palladium complex. This type of chiral auxiliary is widely described in the literature, in particular by Sei Otsuka et al., in Journal of the American Chemical Society 93, pp. 4301 (1971).

Use can also be made of a platinum complex and more particular reference can be made to the works of A. C. Cope [Journal of the American Chemical Society 90, pp. 909 (1968)].

The chiral complex used corresponds more particularly to general formula (X):

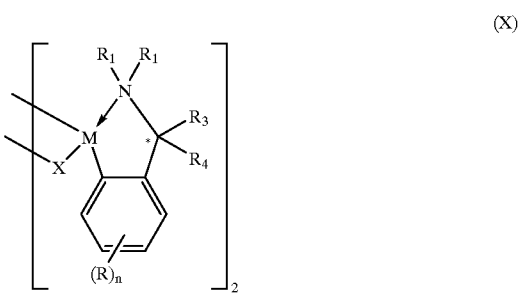

in said formula:

M represents palladium and/or platinum, $R_1$, $R_2$, $R_3$ and $R_4$ represent a hydrogen atom or an alkyl radical having from 1 to 10 carbon atoms or a cycloalkyl radical having from 3 to 10 carbon atoms, $R_3$ and $R_4$ are different and at least one of the two represents a hydrogen atom, R has the meaning given for $R_1$, $R_2$, $R_3$ and $R_4$, X represents a halogen atom, n is a number from 0 to 4, when n is greater than 1, two R radicals and the 2 successive atoms of the benzene ring can together form a ring having from 5 to 7 carbon atoms.

More preferentially, the complex used corresponds to the aforementioned formula in which $R_1$, $R_2$, $R_3$ and R represent a hydrogen atom or a methyl radical, X represents a chlorine atom and n is equal to 0.

When n is equal to 2, two R radicals form a benzene ring.

As more specific examples of palladium complexes suitable for the present invention obtained either from (R)-(+) or (S)-(−)-N,N-dimethylphenylethylamine, there can be mentioned:

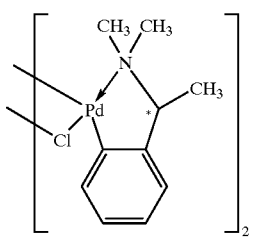

(XI)

The quantity of the aforementioned metal complex expressed in metal is generally from 0.5 to 1 atom of metal per atom of phosphorus.

Use is made of an organic solvent which solubilizes all the reagents. The solvent must be inert vis-à-vis the diphosphine.

As non-limitative examples of solvents which are suitable for the invention process, there can be mentioned aliphatic or aromatic, halogenated or non-halogenated hydrocarbons as mentioned previously.

Among all these solvents, benzene and toluene are preferred.

The concentration of diphosphine in the reaction solvent is preferably between 0.05 and 1 mole/liter and even more particularly between 0.05 and 0.2 mole/liter.

Separation is advantageously carried out at ambient temperature generally comprised between 15° C. and 25° C.

It preferably occurs under a controlled atmosphere of inert gases. An atmosphere of rare gases can be established, preferably argon but it is more economical to use nitrogen.

A mixture of complexes of palladium or platinum and diphosphine is obtained corresponding to each enantiomer.

Another subject of the invention is intermediate products, namely metallic complexes with diphosphines. According to the nature of the substituents, in particular the $R_5$ radical, complexes of the two forms are obtained either corresponding to formulae (XIIa) and (XIIb) or to formulae (XIIIa) and (XIIIb):

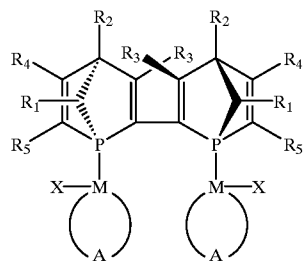

(XIIa)

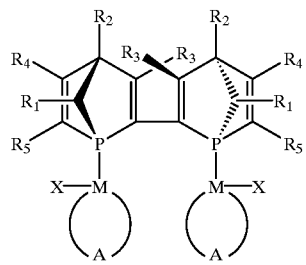

(XIIb)

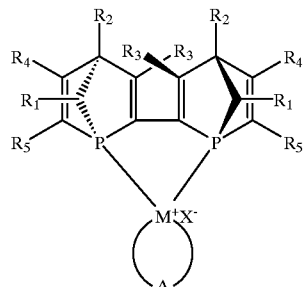

(XIIIa)

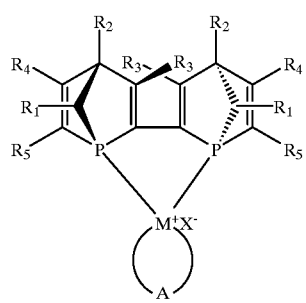

(XIIIb)

in said formulae, M represents palladium or platinum, X represents a halogen atom, preferably chlorine and A symbolizes the remainder of a chiral metallic complex corresponding to one of formulae (X) and preferentially (XI).

In a following stage, the two enantiomers are recovered.

Concentration is carried out by evaporation of the solvent, then separation is carried out in a known manner [A. Bertheillier—Dunod Paris (1972)] using liquid column chromatography, preferably with a silica support.

The column is eluted with a mixture of appropriate solvents.

The solvent or a mixture of solvents is chosen in a standard manner by a person skilled in the art. Ethyl acetate, methanol, hexane, cyclohexane or dichloromethane are generally used as solvents. The examples illustrate the use of a mixture of solvents.

The two isolated enantiomers are recovered in the form of two diastereoisomeric complexes.

The two enantiomers of the diphosphines are recovered by carrying out decomplexing.

For this purpose, a hydrocyanic acid salt is particularly used, preferably an alkaline salt and even more preferentially sodium: said salt being dissolved in the minimum amount of water required.

The complexes are solubilized in an organic solvent such as, for example, dichloromethane, then the hydrocyanic acid salt is introduced under agitation, generally used in an excess representing from 2 to 5 mol per atom of metal.

The operation is also carried out under a controlled atmosphere and at ambient temperature.

The enantiomer is recovered from the organic phase, which is separated, washed with water and dried, for example over sodium sulphate.

Two 6,6'-bis-(1-phosphanorbornadiene) enantiomers are obtained, isolated corresponding to the aforementioned formulae (Ia) and (Ib).

When the optically active diphosphines are prepared according to a sulphur route, the racemic mixture of diphosphine disulphides (IX'r) is resolved on a chiral column, resulting in optically active diphosphine disulphides (IX'a) and (IX'b), then they are reduced to disphosphines, thus leading to optically active diphosphines (Ia) and (Ib).

The diphosphine disulphides are reduced by reaction with a phosphorated reagent of PBu$_3$ or P(CH$_2$CH$_2$CN)$_3$ type: the reaction being carried out in an organic solvent medium, for example an aromatic hydrocarbon, preferably toluene.

The reaction is generally carried out at the reflux temperature of the reaction solvent.

In this way, two enantiomers are obtained:

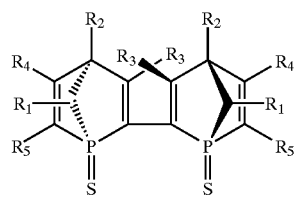

(IX'a)

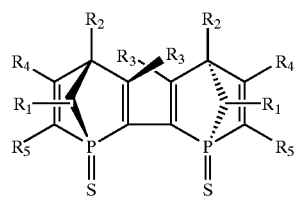

(IX'b)

in formulae (IX'a) and (IX'b), the different symbols have the meaning given previously.

Another variant consists of reducing tire racemic mixture of diphosphine disulphides (IX'r) into a racemic mixture of diphosphines (Ir) then resolving the racemic mixture of diphosphines into optically active phosphines (Ia) and (Ib).

The reduction of the racemic mixture of diphosphine disulphides is carried out in the manner as specified for optically active diphosphine disulphides.

Finally, another variant of the invention consists of converting the racemic mixture of diphosphine disulphides (IX'r) into a racemic mixture of diphosphine dioxides (IXr) then obtaining the optically active diphosphines (Ia) and (Ib) according to the routes specified above.

It is possible to convert the diphosphine disulphides into diphosphine dioxides by any appropriate means, in particular by reacting the diphosphine disulphides with cyclohexene oxide, in trifluoroacetic acid and in an organic solvent medium, in particular in a halogenated aliphatic hydrocarbon, preferably methylene chloride.

The racemic mixture (IXr) is obtained, which is treated as mentioned previously.

The optically active diphosphines according to the present invention are of quite particular use in organic chemistry, in asymmetrical synthesis processes.

The optically active diphosphines according to the invention can be used for the preparation of metallic complexes, allowing asymmetrical hydrogenation of unsaturated derivatives or allylic substitution (Tsuji-Trost type reaction).

More particularly, they can be used to carry out asymmetrical hydrogenation reactions.

The optically active diphosphines according to the invention can be used for the preparation of metallic complexes allowing asymmetrical hydrogenation of a,b-unsaturated carboxylic acids and/or derivatives.

The optically active diphosphines of formula (Ia) or (Ib) serve as ligands in the formation of complex coordinates with transition metals.

A subject of the invention is therefore new complexes which comprise an optically active diphosphine and a transition metal which are characterized in that the ligand corresponds to one of the following formulae (Ia) or (Ib).

As examples of transition metals capable of forming complexes, there can in particular be mentioned metals such as rhodium, ruthenium, rhenium, iridium, cobalt, nckel, platinum, palladium.

Among the above metals, rhodium, ruthenium and iridium are preferred.

Specific examples of said complexes of the present invention are given below, without any limitative character.

In said formulae, (P*P) represents the diphosphine of formula (Ia) or (Ib).

The rhodium and iridium complexes can be represented by the following formulae:

$$[M L_2(P^*P)]Y \qquad (XIVa)$$

$$[M L_2(P^*P)]Y \qquad (XIVb)$$

in said formulae:

(P*P) in formula (XIVa) represents the diphosphine of formula (Ia) and in formula (XIVb) represents the diphosphine of formula (Ib), M represents rhodium or iridium, Y represents a coordinating anionic ligand, L represents a neutral ligand.

The preferred rhodium or iridium complexes correspond to formula (XIVa) or (XIVb) in which:

L represents an olefine having from 2 to 12 carbon atoms and two ligands L can be linked together to form a polyunsaturated, linear or cyclic hydrocarbon chain; L preferably representing 1,5-cyclooctadiene, norbornadiene, ethylene, Y represents a PF$_6^-$, PCl$_6^-$, BF$_4^-$, BCl$_4^-$, SbF$_6^-$, SbCl$_6^-$, BPh$_4^-$, ClO$_4^-$, CN$^-$, CF$_3$SO$_3^-$ anion, preferably halogen, Cl$^-$ or Br$^-$, a 1,3-diketonate, alkylcarbonate, haloalkylcarboxylate anion with a lower alkyl radical, a phenylcarboxylate or phenolate anion the benzene ring of which can be substituted by lower alkyl radicals and/or halogen atoms.

By lower alkyl radicals is generally understood a linear or branched alkyl radical having from 1 to 4 carbon atoms.

Other iridium complexes can be represented by the formulae:

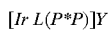 (XVa)

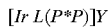 (XVb)

in said formulae, (P*P), L and Y have the meanings given for formulae (XIVa) and (XIVb).

As regards the ruthenium complexes, they preferentially correspond to the following formulae:

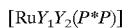 (XVIa)

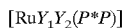 (XVIb)

in said formulae:
- (P*P) in formula (XVIa) represents the diphosphine of formula (Ia) and in formula (XVIb) represents the diphosphine of formula (Ib),
- $Y_1$ and $Y_2$, identical or different, preferably represent a $PF_6^-$, $PCl_6^-$, $BF_4^-$, $BCl_4^-$, $SbF_6^-$, $SbCl_6^-$, $BPh4^-$, $ClO_4^-$, $CF_3SO_3^-$ anion, a halogen atom, more particularly chlorine or bromine or a carboxylate anion, preferentially acetate, trifluoroacetate.

Other ruthenium complexes which may be used in the process according to the invention correspond to the following formulae:

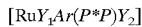 (XVIc)

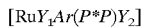 (XVId)

in said formulae:
- (P*P) in formula (XVIc) represents the diphosphine of formula (Ia) and in formula (XVId) represents the diphosphine of formula (Ib),
- Ar represents benzene, p-methylisopropylbenzene, hexamethylbenzene,
- $Y_1$ represents a halogen atom, preferably chlorine or bromine,
- $Y_2$ represents an anion, preferably a $PF_6^-$, $PCl_6^-$, $BF_4^-$, $BCl_4^-$, $SbF_6^-$, $SbCl_6^-$, $BPh_4^-$, $ClO_4^-$, $CF_3SO_3^-$ anion.

It is also possible to use palladium- and platinum-based complexes in the process of the invention.

As more specific examples of said complexes, there can be mentioned among others $PdCl_2(P^*P)$ and $PtCl_2(P^*P)$ in which (P*P) represents the diphosphine of formula (Ia) or (Ib).

The complexes comprising the aforementioned diphosphine and the transition metal can be prepared according to known processes described in the literature.

For the preparation of ruthenium complexes, reference can be made in particular to the publication of J.-P. Genêt [Acros Organics Acta,1, No. 1, pp. 1–8 (1994)] and for the other articles, reference can be made to the article by Schrock R. and Osborn J. A. [Journal of the American Chemical Society, 93, pp. 2397 (1971)].

They can be prepared in particular by reacting the diphosphine of formula (Ia) or (Ib) with the transition metal compound, in an appropriate organic solvent.

The reaction is carried out at a temperature comprised between ambient temperature (from 15 to 25° C.) and the reflux temperature of the reaction solvent.

As examples of organic solvents, there can be mentioned among others aliphatic, halogenated or non-halogenated hydrocarbons and more particularly hexane, heptane, isooctane, decane, benzene, toluene, methylene chloride, chloroform; solvents of ether or ketone type and in particular diethylether, tetrahydrofuran, acetone, methylethylketone; solvents of alcohol type; preferably methanol or ethanol.

The metallic complexes according to the invention, recovered according to standard techniques (filtration or crystallization) are used in asymmetrical hydrogenation reactions of substrates specified below.

Another subject of the present invention is to provide a preparation process for an optically active carboxylic acid and/or derivative, which process is characterized by the fact that asymmetrical hydrogenation is carried out on an a,b-unsaturated carboxylic acid and/or its derivatives in the presence of an effective quantity of a metallic complex comprising as ligand the optically active diphosphine of formula (Ia) or (Ib) and a transition metal.

The a,b-unsaturated carboxylic acid and/or its derivatives correspond more particularly to formula (XVII):

formule (XVII):

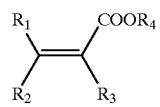 (XVII)

in said formula (XVII):
- $R_1$, $R_2$, $R_3$ and $R_4$ represent a hydrogen atom and any hydrocarbon group, provided that:
  - if $R_1$ is different from $R_2$ and different from a hydrogen atom, then $R_3$ can be any hydrocarbon or functional group designated by R.
  - if $R_1$ or $R_2$ represents a hydrogen atom and if $R_1$ is different from $R_2$, then $R_3$ is different from a hydrogen atom and different from —$COOR_4$,
  - if $R_1$ is identical to $R_2$ and represents any hydrocarbon or functional group designated by R then $R_3$ is different from —CH—(R)2 and different from —$COOR_4$,
- one of groups $R_1$, $R_2$ and $R_3$ can represent a functional group.

The identical or different $R_1$ to $R_4$ radicals represent an optionally substituted hydrocarbon radical having from 1 to 20 carbon atoms, which can be a saturated or unsaturated, linear or branched acyclic aliphatic radical; a saturated, unsaturated or aromatic, monocyclic or polycyclic, carbocyclic or heterocyclic radical; a saturated or unsaturated, linear or branched aliphatic radical carrying a cyclic substituent.

In general formula (XVII), $R_1$ to $R_4$, identical or different, can assume various meanings. Different examples are given below but are in no way limitative.

The $R_1$ to $R_4$ radicals thus preferentially represent an aromatic hydrocarbon radical, and in particular benzenic, corresponding to general formula (XVIII):

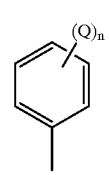 (XVIII)

in said formula (II:

n is an integer from 0 to 5, preferably 0 to 3,

Q represents $R_0$, one of the following groups or functions:
- a linear or branched alkyl radical having from 1 to 6 carbon atoms, preferably 1 to 4 carbon atoms, such as methyl, ethyl, propyl, isopropyl, butyl, isobutyl, sec-butyl, tert-butyl,
- a linear or branched alkenyl radical having from 2 to 6 carbon atoms, preferably 2 to 4 carbon atoms, such as vinyl, allyl,
- a linear or branched alkoxy radical having from 1 to 6 carbon atoms, preferably from 1 to 4 carbon atoms such as the methoxy, ethoxy, propoxy, isopropoxy, butoxy radicals,
- an acyl group having from 2 to 6 carbon atoms,
- a radical of formula:

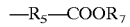

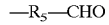

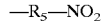

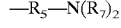

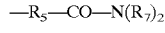

in said formulae, $R_5$ represents a valency bond or a linear or branched, saturated or unsaturated divalent hydrocarbon radical having from 1 to 6 carbon atoms such as, for example, methylene, ethylene, propylene, isopropylene, isopropylidene; $R_7$ represents a hydrogen atom or a linear or branched alkyl radical having from 1 to 6 carbon atoms; X represents a halogen atom, preferably a chlorine, bromine or fluorine atom, Q represents $R_0'$, one of the following more complex radicals:

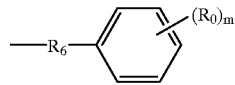

in which:
- m is an integer from 0 to 5, preferably from 0 to 3,
- $R_0$ has the meaning given previously,
- $R_6$ represents a valency bond; a linear or branched, saturated or unsaturated divalent hydrocarbon group having from 1 to 6 carbon atoms such as for example methylene, ethylene, propylene, isopropylene, isopropylidene or one of the following groups referred to as Z: —O—; —CO—; —COO—; —NR$_7$—; —CO—NR$_7$—; —S—; —SO$_2$—; —NR$_7$—CO—;
  in said formulae $R_7$ represents a hydrogen atom, a linear or branched alkyl group having from 1 to 6 carbon atoms, preferably a methyl or ethyl radical.

When n is greater than 1, the radicals Q can be identical or different and 2 successive carbon atoms of the benzene ring can be linked together by a ketal bridge such as the extranuclear methylene dioxy or ethylene dioxy radicals.

Preferably, n is equal to 0, 1, 2 or 3.

Among all the aforementioned $R_1$ to $R_4$ radicals, the following are quite preferentially used in the process of the invention: carboxylic acids or derivatives corresponding to general formula (XVII) in which $R_1$ to $R_4$ represent an aromatic radical corresponding to general formula (XVIII) in which:
- n is equal to 0, 1, 2 or 3,
- Q represents one of the following groups or functions:
  - a hydrogen atom,
  - a linear or branched alkyl radical having from 1 to 4 carbon atoms,
  - a linear or branched alkoxy radical having from 1 to 4 carbon atoms,
  - a benzoyl group,
  - an —OH group,
  - a —CHO group,
  - an NH$_2$ group,
  - an NO$_2$ group,
  - a phenyl radical,
  - a halogen atom,
  - a CF$_3$ group.

Even more preferentially, the compounds of formula (XVII) are chosen in which the Q radicals, identical or different, are a hydrogen atom, an alkyl radical having from 1 to 4 carbon atoms, a methoxy radical, a benzoyl group, an NO$_2$ group.

As examples of $R_1$ to $R_4$ radicals corresponding to formula (XVII), there can more specifically be mentioned the phenyl, tolyl or xylyl; 1-methoxyphenyl, 2-nitrophenyl radicals and the biphenyl, 1,1'-methylenebiphenyl, 1,1'-isopropylidenebiphenyl, 1,1'-carboxybiphenyl, 1,1'-oxybiphenyl, 1,1'-iminobiphenyl radicals: said radicals being able to be substituted by one or more Q radicals as defined previously.

$R_1$ to $R_4$ can also represent a polycyclic aromatic hydrocarbon radical; the rings together being able to form orthocondensed, ortho- and peri-condensed systems. There can more particularly be mentioned a naphthalenic radical; said rings being able to be substituted by 1 to 4 $R_0$ radicals, preferably 1 to 3, $R_0$ having the meanings specified previously for the substituents of the aromatic hydrocarbon radical of general formula (XVIII).

In general formula (XVII) for carboxylic acids, $R_1$ to $R_4$ can also represent a carbocyclic radical which is saturated or comprises 1 or 2 unsaturations in the ring, generally having from 3 to 7 carbon atoms, preferably 6 carbon atoms in the ring; said ring being able to be substituted by 1 to 5 $R_0$ radicals, preferably 1 to 3, $R_0$ having the meanings indicated previously for the substituents of the aromatic hydrocarbon radical of general formula (XVIII).

As preferred examples of $R_1$ to $R_4$ radicals, there can be mentioned the cyclohexyl or cyclohexene-yl radicals, optionally substituted by linear or branched alkyl radicals, having from 1 to 4 carbon atoms.

As mentioned previously, $R_1$ to $R_4$ can represent a saturated or unsaturated, linear or branched acyclic aliphatic radical.

More precisely, $R_1$ to $R_4$ represent a linear or branched acyclic aliphatic radical preferably having from 1 to 12 carbon atoms, saturated or comprising one or more unsaturations on the chain, generally 1 to 3 unsaturations which can be single or conjugated double bonds or triple bonds.

The hydrocarbon chain can optionally be:
- interrupted by one of the following groups Z:
  —O—; —CO—; —COO—; —NR$_7$—; —CO—NR$_7$—; —S—; —SO$_2$—; —NR$_7$—CO—; in said formulae, $R_7$ represents a hydrogen atom, a linear or branched alkyl group having from 1 to 6 carbon atoms, preferably a methyl or ethyl radical,
and/or carrying one of the following substituents: —OH, —COOR$_7$, —CHO, —NO$_2$, —CN, —NH$_2$, —SH, —X, —CF$_3$, in these formulae, $R_7$ has the meaning given previously.

It is also possible to make use of a carboxylic acid or derivative of formula (XVII) in which $R_1$ to $R_4$ represent a saturated or unsaturated, linear or branched acyclic aliphatic radical which can optionally carry a cyclic substituent. By ring is understood a saturated, unsaturated or aromatic carbocyclic or heterocyclic ring.

The acyclic aliphatic radical can be linked to the ring by a valency bond or by one of the aforementioned groups Z.

As examples of cyclic substituents, there can be envisaged cycloaliphatic, aromatic or heterocyclic substituents, in particular cycloaliphatic substituents comprising 6 carbon atoms in the ring or benzene substituents, these cyclic substituents themselves being optional carriers of 1, 2, 3, 4 or 5 $R_0$ radicals, identical or different, $R_0$ having the meanings indicated previously for the substituents of the aromatic hydrocarbon radical of general formula (XVIII).

As examples of such radicals, there can be mentioned, amongst others, the benzyl radical.

In general formula (XVII) for carboxylic acids, $R_1$ to $R_4$ can also represent a a saturated or unsaturated heterocyclic radical in particular comprising 5 or 6 atoms in the ring including 1 or 2 heteroatoms such as the nitrogen, sulphur and oxygen atoms; the carbon atoms of the heterocycle being optionally substituted, totally or only partially by the $R_0$ radicals, $R_0$ having the meanings indicated previously for substituents of the aromatic hydrocarbon radical of general formula (XVIII).

$R_1$ to $R_4$ can also represent a polycyclic heterocyclic radical defined as being either a radical constituted by at least 2 aromatic or non-aromatic heterocycles containing at least one heteroatom in each ring and together forming ortho- or ortho- and peri-condensed systems or a radical constituted by at least one aromatic or non-aromatic hydrocarbon ring and at least one aromatic or non-aromatic heterocycle together forming ortho- or ortho- and peri-condensed systems; the carbon atoms of said rings being optionally substituted, totally or only partially, by $R_0$ radicals, $R_0$ having the meanings indicated previously for the substituents of the aromatic hydrocarbon radical of general formula (XVIII).

As examples of $R_1$ to $R_4$ groups of heterocyclic type, there can be mentioned among others the furyl, pyrrolyl, thienyl, isoxazolyl, furazannyl, isothiazolyl, imidazolyl, pyrazolyl, pyridyl, pyridazinyl, pyrimidinyl, pyrannyl radicals and the quinolyl, naphthyridinyl, benzopyrannyl, benzofurannyl, indolyl radicals.

It is also possible for one of the $R_1$ to $R_3$ radicals to represent a functional group and there can be mentioned in particular the functional groups of type NR$_9$R'$_9$ in which $R_9$, R'$_9$, identical or different, represent a hydrogen atom, a linear or branched alkyl group having from 1 to 12 carbon atoms, a phenyl group, a benzyl group or an acyl group having from 2 to 12 carbon atoms, preferably an acetyl or benzoyl group.

As a more specific example, there can be mentioned amongst others 2-methyl-2-butenoic acid.

A first class of substrates to which the process of the invention preferentially relates is the substituted acrylic acid precursors of amino acids and/or derivatives.

By substituted acrylic acids is understood all compounds the formula of which derives from that of acrylic acid, substituting up to two hydrogen atoms carried by ethylenic carbon atoms with a hydrocarbon group or with a functional group.

They can be symbolized by the following chemical formula:

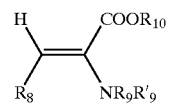

(XVIIa)

in said formula (XVIIa):
$R_9$, R'$_9$, identical or different, represent a hydrogen atom, a linear or branched alkyl group having from 1 to 12 carbon atoms, a phenyl group or an acyl group having from 2 to 12 carbon atoms, preferably an acetyl or benzoyl group, $R_8$ represents a hydrogen atom, an alkyl group having from 1 to 12 carbon atoms, a cycloallyl radical having from 3 to 8 carbon atoms, an arylalkyl radical having from 6 to 12 carbon atoms, an aryl radical having from 6 to 12 carbon atoms, a heterocyclic radical having from 4 to 7 carbon atoms, $R_{10}$ represents a hydrogen atom or a linear or branched alkyl group having from 1 to 4 carbon atoms.

As more specific examples of $R_8$ groups, there can be mentioned an alkyl group such as methyl, ethyl, isopropyl, isobutyl; a cycloalkyl group such as cyclopentyl, cyclohexyl; an aromatic group such as phenyl, naphthyl or a heterocyclic group such as furyl, pyrannyl, benzopyrannyl, pyrrolyl, pyridyl, indolyl.

The $R_{10}$ group is preferentially a hydrogen atom.

Among the substituted acrylic acids which are precursors of amino acids, there can be mentioned N-acetyl a-amino b-phenylacrylic acid, N-benzoyl a-amino b-phenylacrylic acid, in which the phenyl ring is optionally substituted by one or more alkyl, alkoyloxy or hydroxy groups, N-acetyl a-amino b-indolylacrylic acid, N-benzoyl a-amino b-indolylacrylic acid, N-acetyl a-amino b-isobutyl acrylic acid.

There can more particularly be mentioned:
methyl a-acetamidocinnamate,
methyl acetamidoacrylate,
benzamidocinnamic acid,
a-acetamidocinnamic acid.

The invention also relates equally well to the hydrogenation of itaconic acid and/or a derivative, and more specifically to compounds corresponding to formula (XVIIb):

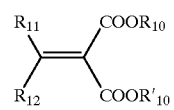

(XVIIb)

in said formula (XVIIb):
$R_{11}$, $R_{12}$, identical or different, represent a hydrogen atom, a linear or branched alkyl group having from 1 to 12 carbon atoms, a cycloalkyl radical having from 3 to 8 carbon atoms, an arylalkyl radical having from 6 to 12 carbon atoms, an aryl radical having from 6 to 12 carbon atoms, an aryl radical having from 6 to 12 carbon atoms, a heterocyclic radical having from 4 to 7 carbon atoms, $R_{10}$, $R'_{10}$, identical or different, represent a hydrogen atom or a linear or branched alkyl group, having from 1 to 4 carbon atoms.

The preferred substrates correspond to formula (XVIIb) in which $R_{11}$, $R_{12}$, identical or different, represent a hydrogen atom, an alkyl group having from 1 to 4 carbon atoms and $R_{10}$, $R'_{10}$, identical or different, represent a hydrogen atom or a methyl group.

As more specific examples, there can be mentioned in particular itaconic acid and dimethyl itaconate.

The process of the invention relates quite particularly to the preparation of arylpropionic acids by hydrogenation of a substrate corresponding to formula (XVIIc):

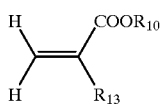

(XVIIc)

in said formula (XVIIc):
- $R_{10}$ represents a hydrogen atom or a linear or branched alkyl group having from 1 to 4 carbon atoms,
- $R_{13}$ represents a phenyl or naphthyl group, optionally carrying a substituent or several substituents R:
  - R can represent $R_0$, one of the following groups:
    - a linear or branched alkyl or alkenyl group having from 1 to 12 carbon atoms, preferably a linear or branched alkyl group having from 1 to 4 carbon atoms,
    - a linear or branched alkoxy group having from 1 to 12 carbon atoms, preferably a linear or branched alkoxy group having from 1 to 4 carbon atoms,
    - a linear or branched acyloxy group having from 2 to 8 carbon atoms, preferably an acetoxy group,
    - a linear or branched acylamido group having from 1 to 8 carbon atoms, preferably an acetamido group,
    - an $NO_2$ group,
  - R can represent $R_0'$, one of the following more complex groups:
    - a group of formula

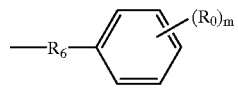

in which:
- $R_6$ represents a valency bond; a linear or branched, saturated or unsaturated divalent hydrocarbon group, such as for example methylene, ethylene, propylene, isopropylene, isopropylidene or one of the following groups referred to as Z:
  —O—; —CO—; —COO—; —$NR_7$—; —CO—$NR_7$—; —S—; —$SO_2$—; —$NR_7$—CO—;
  in said formulae, $R_7$ represents a hydrogen atom, a linear or branched alkyl group having from 1 to 6 carbon atoms,
- $R_0$ has the meaning given previously,
- m is an integer from 0 to 4.

As specific examples, there can be mentioned 2-(3-benzoylphenyl)propionic acid (Ketoprofen®), 2-(4-isobutylphenyl)propionic acid (Ibuprofen®), 2-(5-methoxynaphthyl)propionic acid (Naproxen®).

Selective asymmetrical hydrogenation of said substrates is carried out using as catalysts the metallic complexes of the invention liganded by optically active diphosphines of general formula (Ia) or (Ib).

When the diphosphine-transition metal complexes of the invention are used as asymmetrical hydrogenation catalysts of unsaturated carboxylic acids, the desired product can be obtained with a high optical yield.

By choosing one of the diphosphine optical isomers having a (+) or (−) rotatory power, and using a diphosphine-transition metal complex comprising the chosen isomer, the unsaturated carboxylic acid is hydrogenated into a compound having the desired absolute configuration, with a high optical yield.

Hydrogenation is generally carried out at a temperature comprised between 20 and 100° C.

The hydrogen pressure can be comprised between 0.1 and 200 bar, and more preferentially between 1 and 150 bar.

The diphosphine/transition metal complex is used in such a manner that the ratio between the number of atoms of metal present in the complex and the number of moles of the compound to be hydrogenated is comprised between 0.1 and 0.0001.

The hydrogenation process is preferably implemented in an organic solvent. Any type of solvent is used provided it is stable under the reaction conditions.

A polar organic solvent is preferably used, and more particularly the following solvents:
- aliphatic, cycloaliphatic or aromatic ether-oxides, and more particularly diethylether, dipropylether, diisopropylether, dibutylether, methyltertiobutylether, ditertiobutylether, ethyleneglycol dimethylether, diethyleneglycol dimethylether; diphenylether, dibenzylether, anisole, phenetole, 1,4-dimethoxybenzene, veratrole, 1,4-dioxane, tetrahydrofuran (THF),
- mono- or polyhydroxylated alcohols and more particularly aliphatic monoalcohols such as methanol, ethanol, propanol, butanol, sec-butanol, tert-butanol, pentanol, hexanol, aliphatic dialcohols such as ethylene glycol, diethylene glycol, propylene glycol, cycloaliphatic alcohols such as cyclopentanol, cyclohexanol,
- aliphatic ketones such as acetone, methylethylketone, diethylketone,
- aliphatic esters such as in particular methyl acetate, ethyl acetate, propyl acetate.

The concentration of the substrate in the organic solvent advantageously varies between 0.01 and 1 mol/l.

After the formation of the hydrogenation complex, a basic compound can optionally be added.

This basic compound can be an alkaline base such as sodium or potassium hydroxide or a primary, secondary or tertiary amine, and more particularly pyridine, piperidine, triethylamine and preferably triethylamine.

The quantity of base added is such that the ratio between the number of moles of base and the number of metallic atoms present in the diphosphine/transition metal complex is comprised between 0 and 25, preferably between 0 and 12.

There follows a preferential implementation of the process of the invention.

Said process is implemented in an autoclave which is purged using an inert gas, preferably nitrogen. The substrate is preferably loaded in the organic solvent, then the catalyst also in solution in the organic solvent.

The nitrogen is replaced with hydrogen.

Hydrogenation is completed when the hydrogen pressure becomes stable.

The hydrogenation process according to the invention provides access to the different enantiomers of numerous derivatives.

As mentioned previously, the implementation of new diphosphines according to the invention allows an improvement in the enantiomeric excess in certain asymmetrical catalysis reactions, in particular in allylic substitution reactions [M. YAMAGUSI et al., Tetrahedron Letters, 31, p. 5049 (1990) and [M. MAYASHI et al., Tetrahedron Letters 27, p. 191 (1986)].

As more specific examples illustrating this type of reaction, there can more particularly be mentioned the reaction of esters, preferably 1,3-diphenyl-3-acetoxypropene with alkyl esters of malonic acid, preferably dimethyl or diethyl malonate.

The reaction is carried out in the presence of a complex comprising an optically active diphosphine and palladium: the ligand corresponding to one of the following formulae (Ia) or (Ib).

The palladium precursor preferentially chosen corresponds to the formula [Pd(allyl)Cl]$_2$.

The reaction is preferably carried out in a polar aprotic solvent, in particular an aliphatic or aromatic halogenated hydrocarbon or in a solvent of nitrile type, preferably acetonitrile, an aliphatic, cycloaliphatic or aromatic ether oxide, and more particularly diethyl oxide, dipropyl oxide, diisopropyl oxide, dibutyl oxide, methyltertiobutylether, dipentyl oxide, diisopentyl oxide, ethyleneglycol dimethylether (or 1,2-dimethoxyethane), diethyleneglycol dimethylether (or 1,5-dimethoxy 3-oxapentane); benzyl oxide; dioxane, tetrahydrofuran (THF).

Among said solvents, tetrahydrofuran is preferentially used.

The quantity of organic solvent used can vary very widely. The ratio between the number of moles of solvent and the number of-moles of substrate can thus range from 10 to 40 and is preferably comprised between 20 and 25.

The molar ratio of the malonic acid ester/unsaturated substrate generally varies between 1 and 5, preferably between 1 and 3.

The malonic acid ester which is reacted can be in the form of an anion. For this purpose, before reaction with the substrate, it is reacted with a nucleophile, preferably sodium hydride.

The hydride is used in a quantity ranging from the stoichiometric quantity to an excess, for example of 20%.

The reaction is advantageously carried out at low temperature, preferably between −10° C. and 10° C., preferably in the region of 0° C.

From a practical point of view, the malonic ester anion is first formed by reacting the malonic ester with sodium hydride, followed by adding the substrate and the catalyst previously obtained by reacting the palladium salt and the ligand, in an organic solvent, preferably tetrahydrofuran.

The reaction is advantageously carried out at ambient temperature, i.e. at a temperature generally ranging from 15° C. to 25° C.

The coupling product is obtained in allylic position.

The following examples illustrate the invention without however limiting it.

In Examples 1 to 4, new diphosphines are prepared.

Examples 5, 7 and 8 relate to the preparation of catalysts which are implemented in application Examples 6, 9 and 10.

EXAMPLE 1

In this example, a diphosphine corresponding to the following formula is prepared:

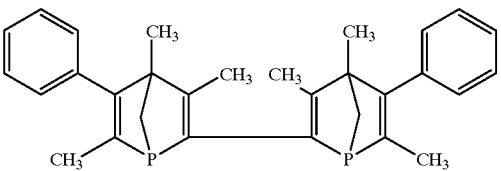

Phospholyllithium 11.3 g (0.6 mol) of 1-phenyl-3,4-dimethylphosphole, 0.8 g of lithium metal and 10 ml of distilled tetrahydrofuran are introduced into a 250 ml flask.

The mixture is agitated under argon for 2 hours, in a cold water bath.

The solution becomes brown.

The appearance of phospholyllithium is checked by NMR $^{31}$P.

NMR $^{31}$P: δ(THF)=55.8 ppm.

In order to trap the phenyllithium, 2.7 g of aluminium chloride is added at 0° C.

The medium is left to react for 30 minutes at 0° C.
1,1'-bis-(3,4-dimethylphosphole) (IV)

6 g (0.025 mol) of iodine in solution in 25 ml of tetrahydrofuran is added dropwise at ambient temperature to the preceding mixture.

When 90% of this solution is introduced, the disappearance of (III) is verified by NMR $^{31}$P.

NMR $^{31}$P: δ(THF)=−22.4 ppm. The 1,1'-bis-(3,4-dimethylphosphole) is extracted from the mixture using hexane.
6,6'bis-(1-phospha-3 phenyl-2,4,5-trimethylnorbornadiene) in Meso Form (Im) and in Racemic Form (Ir)

The previous solution is evaporated to dryness, sheltered from the air and taken to 140° C.

Then 5.2 g of methylphenylacetylene is introduced and the medium is left to react for 15 to 20 minutes.

The disappearance of 1,1'-bis-(3,4-dimethylphosphole) is again monitored by NMR $^{31}$P.

The spectrum is composed of 2 singlets corresponding to two diastereoisomers.

NMR $^{31}$P: δ(CH$_2$Cl$_2$)=−13.2 ppm (Im)
NMR $^{31}$P: δ(CH$_2$Cl$_2$)=−13.5 ppm (Ir)

The product is extracted with ether and washed with water.

The organic phases are combined then evaporated to dryness.

The residue is then purified by chromatography on a silica column (elution with hexane in order to eliminate the excess methylphenylacetylene then with a mixture of hexane/dichloromethane: 80/20 by volume).

The overall yield is 30%.
6,6'bis-(1-phospha-3-phenyl-2,4,5-trimethylnorbornadiene) dioxide in Meso Form (IXm) and in Racemic Form (IXr)

The (Im)+(Ir) mixture obtained previously is dissolved in 50 ml of toluene and oxidized with 10 ml of a hydrogen peroxide solution at 30% by weight of hydrogen peroxide introduced in excess. The mixture is then heated at 70° C. for 2 hours under mechanical agitation.

The disappearance of (Im)+(Ir) is again monitored by NMR $^{31}$P.

After cooling down the aqueous phase is decanted. The organic solution is washed once with sodium thiosulphate (10 ml of saturated solution) and once with water (10 ml).

After drying over sodium sulphate and evaporation of the solvent, an oil is recovered the NMR $^{31}$P spectrum of which is constituted by a mixture of two diastereoisomers (IXm) and (IXr).

NMR $^{31}$P: δ(CH$_2$Cl$_2$)=50.2 ppm (IXm)
NMR $^{31}$P: δ(CH$_2$Cl$_2$)=53.1 ppm (IXr)

The two diastereoisomers are separated by chromatography on a silica column with elution with ethyl acetate then a mixture of ethyl acetate/methanol (90/10 by volume).

The overall yield of (IXm)+(IXr) is 90%.

Reduction of (IXr) to Diphosphine (Ir)

1.55 g (0.003 mol) of racemic (IXr) and 10 ml of toluene are introduced into a 100 ml flask.

1.42 of distilled pyridine is added at ambient temperature, then 0.81 g of trichlorosilane is added dropwise and the mixture is heated for 10 minutes at 80° C. The reaction is monitored by NMR $^{31}$P.

The excess trichlorosilane is neutralized with an aqueous solution of soda at 30% by weight, then the aqueous phase is extracted three times with ether, the organic phases are combined then washed with a saturated solution of sodium chloride.

The organic phase is dried over magnesium sulphate and evaporated under reduced pressure.

The phosphine (Ir) thus obtained is purified on a column of deactivated silica gel (elution dichloromethane).

The overall yield of the reduction is 95%.

The characterization of the racemic mixture (Ir) is as follows:

NMR $^{31}$P: δ(toluene)=−13.5 ppm
NMR $^1$H: δ(CDCl$_3$)=1.02 (s, 6H, CH$_3$); 1.4–2.1 (m, 16H, CH$_2$ bridge, CH$_3$); 6.8–7.4 (m, 20 H, phenyl).

Binuclear Complex of Palladium II (XIIa) and (XIIb)

243 mg (0.5 mmol) of racemic (Ir) and 300 mg (0.05 mmol) of (−)-di-μ-chloro- bis[(S)-N,N-dimethyl-α-phenylethylamine-2C,N)]dipalladium II are introduced into 12 ml of toluene.

Complexing is rapid and is followed by NMR $^{31}$P.

The brown solution is evaporated to dryness and the residue is chromatographed in order to separate the two diastereoisomers (elution toluene/ethyl acetate: 90/10 by volume).

In this way the two pure isolated enantiomers are recovered in the form of two diastereoisomer complexes of formula (XIIa) and (XIIb).

NMR $^{31}$P: δ(toluene)=54.3 ppm (XIIa)
NMR $^{31}$P: δ(toluene)=47.8 ppm and 43.2 ppm (XIIb)

Decomplexing of (XIIa) or (XIIIb)

270 mg of (XIIa) (0.25 mmol) and 10 ml of dichloromethane are introduced into a 100 ml flask.

Then 0.5 g of sodium cyanide and a few milliliters of water (3 ml) are added.

Vigorous agitation is carried out under argon for 10 to 15 minutes.

The diphosphine (Ia) is then extracted with dichloromethane.

The organic phase is washed with water then dried over sodium sulphate.

In this way pure (Ia) of formula is recovered.

The overall yield for the separation of diastereoisomers is 90%.

NMR $^{31}$P: δ(CDCl$_3$)=−13.5 ppm [α]$_D$=+57° (c=1, CH$_2$Cl$_2$) (Ia)
NMR $^{31}$P: δ(CDCl$_3$)=−13.5 ppm [α]$_D$=+55° (c=1, CH$_2$Cl$_2$) (Ib)

EXAMPLE 2

In this example, a diphosphine is prepared corresponding to the following formula:

Phospholyllithium

It is prepared according to the operating method of Example 1.

1,1'-bis-(3,4-dimethylphosphole) (IV)

It is synthesized as in Example 1.

6,6'bis-(1-phospha-3 phenyl-4,5-dimethylnorbornadiene) in Meso Form (Im) and in Racemic Form (Ir)

The previous solution is evaporated to dryness, sheltered from the air and taken to 140° C.

Then 4.6 g of phenylacetylene is introduced and the medium is left to react for 15 to 20 minutes.

The disappearance of 1,1'-bis-(3,4-dimethylphosphole) is again monitored by NMR $^{31}$P.

The spectrum is composed of 2 singlets corresponding to two diastereoisomers.

NMR $^{31}$P: δ(toluene)=−30.0 ppm (Ir)
NMR $^{31}$P: δ(toluene)=−29.5 ppm (Im)

The product is extracted with ether and washed with water.

The organic phases are combined then evaporated to dryness.

The residue is then purified by chromatography on a silica column (elution with hexane in order to eliminate the excess phenylacetylene then with a mixture of hexane/dichloromethane: 80/20 by volume).

The overall yield is 25%.

6,6'bis-(1-phospha-3-phenyl-4,5-dimethylnorbornadiene) dioxide in Meso Form (IXm) and in Racemic Form (IXr)

The Im+Ir mixture obtained previously is dissolved in 50 ml of toluene and oxidized with 10 ml of a hydrogen peroxide solution at 30% by weight of hydrogen peroxide introduced in excess. The mixture is then heated at 70° C. for 30 minutes under mechanical agitation.

The disappearance of (Im)+(Ir) is again monitored by NMR $^{31}$P.

After cooling down the aqueous phase is decanted. The organic solution is washed once with a saturated solution of sodium thiosulphate (10 ml) and once with water (10 ml).

After drying over sodium sulphate and evaporation of the solvent, an oil is recovered the NMR $^{31}$P spectrum of which is constituted by a mixture of two diastereoisomers (IXm) and (IXr).

NMR $^{31}$P: δ(toluene)=47.3 ppm (IXr)
NMR $^{31}$P: δ(toluene)=45.8 ppm (IXm)

The two diastereoisomers are separated by chromatography on a silica column with elution with ethyl acetate then a mixture of ethyl acetate/methanol (90/10 by volume).

The overall yield of (IXm)+(IXr) is 90%.

Reduction of (IXr) to Diphosphine (Ir)

1.46 g (0.003 mol) of racemic (IXr) and 10 ml of toluene are introduced into a 100 ml flask.

2.4 of distilled pyridine is added at ambient temperature, then 1.1 g of trichlorosilane is added dropwise and the mixture is heated for 10 minutes at 80° C. The reaction is monitored by NMR $^{31}$P.

The excess trichlorosilane is neutralized with an aqueous solution of soda at 30% by weight, then the aqueous phase is extracted three times with ether, the organic phases are combined then washed with a saturated solution of sodium chloride.

The organic phase is dried over magnesium sulphate and evaporated under reduced pressure.

The phosphine (Ir) thus obtained is purified on a column of deactivated silica gel (elution dichloromethane).

The overall yield of the reduction is 95%.

The characterization of the racemic mixture (Ir) is as follows:

NMR $^{31}$P: δ(toluene)=−30.0 ppm
NMR $^1$H: δ(CDCl$_3$)=1.42 (s, 6H, CH$_3$); 1.82 (s, 6H, CH$_3$); 2.04–2.11 (m, 4H, CH$_3$); 6.85 (d, 2H, $^2$J(H-P)=44Hz); 7.1–7.4 (m, 10H, Ph).).

Binuclear Complex of Palladium II (XIIa) and (XIIIb)

215 mg (0.5 mmol) of racemic (Ir) and 300 mg (0.05 mmol) of (+)-di-μ-chloro-bis[(S)-N,N-dimethyl-α-phenylethylamine-2C,N)]dipalladium II are introduced into 12 ml of toluene under nitrogen.

Complexing is rapid and is followed by NMR $^{31}$P.

The brown solution is evaporated to dryness and the residue is chromatographed in order to separate the two diastereoisomers (elution toluene/ethyl acetate: 90/10 by volume).

In this way the two pure isolated enantiomers are recovered in the form of two diastereoisomer complexes of formula (XIIa) and (XIIIb).

NMR $^{31}$P: δ(toluene)=37.4 ppm $[α]_D$=−77° (c=1, CH$_2$Cl$_2$) (XIIa)
NMR $^{31}$P: δ(toluene)=33.1 ppm and 25.2 ppm $[α]_D$=+89° (c=1, CH$_2$Cl$_2$) (XIIIb)

Decomplexing of (XIIa) or (XIIIb)

250 mg of (XIIa) (0.25 mmol) and 10 ml of dichloromethane are introduced into a 100 ml flask.

Then 0.5 g of sodium cyanide and a few milliliters of water (3 ml) are added.

Vigorous agitation is carried out under argon for 10 to 15 minutes.

The diphosphine (Ia) is then extracted with dichloromethane.

The organic phase is washed with water then dried over sodium sulphate.

In this way pure (Ia) of formula

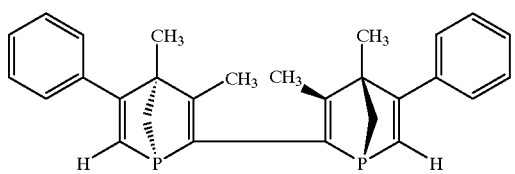

is recovered.

The overall yield of the decomplexing is 90%.

NMR $^{31}$P: δ(CDCl$_3$)=−30.0 ppm $[α]_D$=+205.7° (c=1, CH$_2$Cl$_2$) (Ia)
NMR $^{31}$P: δ(CDCl$_3$)=−30.0 ppm $[α]_D$=−200.2° (c=1, CH$_2$Cl$_2$) (Ib)

EXAMPLE 3

In this example, a diphosphine is prepared corresponding to the following formula:

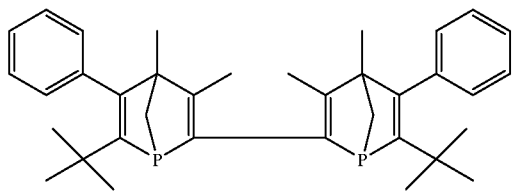

Phospholyllithium

It is prepared according to the operating method of Example 1.

1,1'-bis-(3,4-dimethylphosphole) (IV)

It is synthesized as in Example 1.

6,6'bis-(1-phospha-2-tert-butyl-3-phenyl-4,5-dimethylnorbornadiene) in Meso Form (Im) and in Racemic Form (Ir)

10 g of tert-butylacetylene is reacted with 7 g of 1,1'-bis-(3,4-dimethylphosphole) and the medium is left to react for 15 minutes at 140° C.

6,6'bis-(1-phospha-2-tert-butyl-3-phenyl-4,5-dimethylnorbornadiene) dioxide in Meso Form (IXm) and in Racemic Form (IXr)

The (Im)+(Ir) mixture obtained previously is dissolved in 50 ml of toluene and oxidized with 4.5 g of a hydrogen peroxide solution at 30% by weight of hydrogen peroxide introduced in excess. The mixture is then heated at 70° C. for 3 hours under mechanical agitation.

The disappearance of (Im)+(Ir) is again monitored by NMR $^{31}$P.

After cooling down the aqueous phase is decanted. The organic solution is washed once with sodium thiosulphate (10 ml of saturated solution) and once with water (10 ml).

After drying over sodium sulphate and evaporation of the solvent, an oil is recovered (overall yield=26%) the NMR $^{31}$P spectrum of which is constituted by a mixture of two diastereoisomers (IXm) and (IXr).

NMR $^{31}$P: δ(CH$_2$Cl$_2$)=49.7 ppm (IXr)
NMR $^{31}$P: δ(CH$_2$Cl)=49.9 ppm (IXm)

The two diastereoisomers are separated by chromatography on a silica column with elution with ethyl acetate then a mixture of ethyl acetate/methanol (95/05 by volume).

The overall yield of (IXm)+(IXr) is 100%.

Reduction of (IXr) to Diphosphine (Ir)

The reduction of 1.2 g of diphosphine dioxide (IXr) is carried out.

The phosphine (Ir) thus obtained is purified on a column of deactivated silica gel (elution dichloromethane).

The overall yield of the reduction is 89%.

Binuclear Complex of Palladium II (XIIa) and (XIIIb)

1.24 g (1.87 mmol) of racemic (Ir) and 1 g (1.87 mmol) of (−)-di-μ-chloro-bis[(S)-N,N-dimethyl-α-phenylethylamine-2C,N)]dipalladium II are introduced into 12 ml of toluene.

1.87 g of palladium complexes are obtained.

The diastereoisomers are separated by chromatography on silica gel with a toluene/ethyl acetate mixture 90/10).

0.85 g of complex (XIIa) (yield=45%) and 0.8 g of complex (XIIIb) (yield=44%) are recovered with the following NMR characteristics:

NMR $^{31}$P: δ(CH$_2$Cl$_2$)=36.7 ppm $[α]_D$=61.7° (c=9.3, CH$_2$Cl$_2$) (XIIa)
NMR $^{31}$P: δ(CH$_2$Cl$_2$)=36.72 ppm $[α]_D$=−317.1° (c=10.6, CH$_2$Cl$_2$) (XIIIb)

Decomplexing of (XIIa) or (XIIb)

A decomplexing is carried out with sodium cyanide, in dichloromethane, as described previously.

The diphosphine (Ia) is then extracted with dichloromethane.

The organic phase is washed with water then dried over sodium sulphate.

In this way the compound of formula

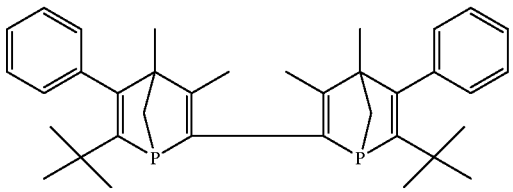

is recovered.

The overall yield of the decomplexing is 85%.

NMR $^{31}$P: δ(toluene)=−17.3 ppm $[α]_D$=+6° (c=1, CH$_2$Cl$_2$)

NMR $^{31}$P: δ(toluene)=−17.3 ppm $[α]_D$=−6° (c=1, CH$_2$Cl$_2$)

EXAMPLE 4

In this example a diphosphine is prepared corresponding to the following formula:

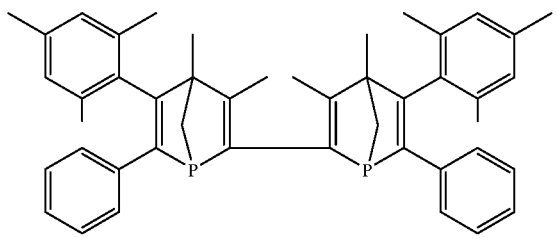

Phospholyllithium

It is prepared according to the operating method of Example 1.

1,1'-bis-(3,4-dimethylphosphole) (IV)

It is synthesized as in Example 1.

6,6'-bis-(1-phospha-2-phenyl-3-mesityl-4,5-dimethylnorbornadiene) in Meso Form (Im) and in Racemic Form (Ir)

14 g of mesitylphenylacetylene (63.3 mmol) is reacted with 7 g of 1,1'-bis-(3,4-dimethylphosphole) (31.65 mol) and the medium is left to react for 15 minutes at 140° C.

6,6'-bis-(1-phospha-2-phenyl-3-mesityl-4,5-dimethylnorbornadiene) dioxide in Meso Form (IXm) and in Racemic Form (IXr)

The (Im)+(Ir) mixture obtained previously is dissolved in 50 ml of toluene and oxidized with 4.6 g of a hydrogen peroxide solution at 30% by weight of hydrogen peroxide introduced in excess. The mixture is then heated at 70° C. for 3 hours under mechanical agitation.

The disappearance of (Im)+(Ir) is again monitored by NMR $^{31}$P.

After cooling down the aqueous phase is decanted. The organic solution is washed once with sodium thiosulphate (10 ml of saturated solution) and once with water (10 ml).

After drying over sodium sulphate and evaporation of the solvent, 4.6 g of an oil is recovered (overall yield=21%) the NMR $^{31}$P spectrum of which is constituted by a mixture of two diastereoisomers (IXm) and (IXr).

NMR $^{31}$P: δ(toluene)=47.4 ppm (IXr)
NMR $^{31}$P: δ(toluene)=48.4 ppm (IXm)

The two diastereoisomers are separated by chromatography on a silica column with elution with ethyl acetate then a mixture of ethyl acetate/methanol (95/05 by volume).

The overall yield of (IXm)+(IXr) is 100%.

Reduction of (IXr) to Diphosphine (Ir)

The reduction of 1.2 g of diphosphine dioxide (IXr) is carried out.

The phosphine (Ir) thus obtained is purified on a column of deactivated silica gel (elution dichloromethane).

The overall yield of the reduction is 90%.

Binuclear Complex of Palladium II (XIIa) and (XIIb)

1.2 g (1.7 mmol) of racemic (Ir) and 0.8 g (1.7 mmol) of (−)-di-μ-chloro-bis[(S)-N,N-dimethyl-α-phenylethylamine-2C,N)]dipalladium II are introduced into 12 ml of toluene.

1.74 g of palladium complexes are obtained.

The diastereoisomers are separated by chromatography on silica gel with a toluene/ethyl acetate mixture (90/10).

The following are recovered:

0.8 g (yield=45%) of an optically active complex (XIIa) having the following characteristics:
NMR $^{31}$P: δ(CH$_2$Cl$_2$)=59.2 ppm $[α]_D$=+300° (c=11.1, CH$_2$Cl$_2$)

and 0.75 g (yield=44%) of an optically active complex (XIIIb) having the following characteristics:
NMR $^{31}$P: δ(CH$_2$Cl$_2$)=58.1 ppm $[α]_D$=−280° (c=10, CH$_2$Cl$_2$)

Decomplexing of (XIIa) or (XIIIb)

A decomplexing is carried out with sodium cyanide, in dichloromethane, as described previously.

The diphosphine is then extracted with dichloromethane.

The organic phase is washed with water then dried over sodium sulphate.

In this way the compound of formula

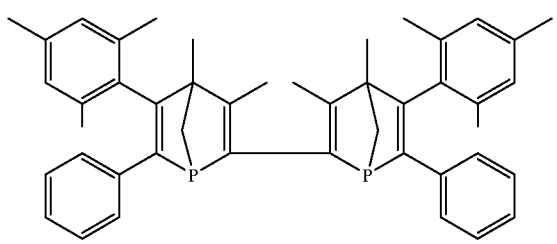

is recovered.

The overall yield of the decomplexing is 85%.

NMR $^{31}$P: δ(toluene)=−9.5 ppm $[α]_D$=+114° (c=9.5, CH$_2$Cl$_2$)

NMR $^{31}$P: δ(toluene)=−9.5 ppm $[α]_D$=−114° (c=9.5, CH$_2$Cl$_2$)

EXAMPLE 5

In this example, the preparation of a complex of formula [Rh$^+$(COD)(P*P)]PF$_6^-$ is described in which COD represents 1,5-cyclooctadiene and (P*P) represents the diphosphine of formula (Ia) of Example 1.

11.6 mg of Rh(COD)$_2$PF$_6$ is dissolved under argon in 3 ml of acetone in a 10 ml schlenk tube.

A solution of 11.3 mg of said diphosphine in acetone is then added dropwise, still under an inert gas atmosphere.

After agitation for a few minutes, the expected complex is obtained.

NMR $^{31}$P: δ=−61.6 ppm, J(Rh-P)=155 Hz.

EXAMPLE 6

In this example, the asymmetrical hydrogenation of the following compound is carried out, using the catalyst of Example 5:

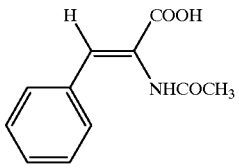

400 mg of said compound is dissolved in a flask in 20 ml of methanol.

Then, the metallic complex as proposed in Example 5 is prepared.

The acetone is evaporated off and the residue is dissolved in 5 ml of methanol.

Then, the two solutions are introduced into an autoclave which has been purged beforehand and maintained under a nitrogen atmosphere.

Then, hydrogen is introduced up to a pressure of 3 atmospheres.

Agitation is carried out for 1 hour at 20° C.

The excess hydrogen is removed and the reaction solution is recovered.

The solvent is evaporated off and the residue analyzed by NMR$^1$H in order to verify the progress of the reaction.

The reaction is quantitative.

The enantiomeric excess is determined by chiral high performance liquid chromatography (chiral protein HSA column 150×6.4 mm Shandon®) and the absolute configuration of the product by measurement of the $\alpha_D$ by polarimetry.

With the diphosphine of Example 1, ee=35%, $[\alpha_D]$ (ethanol, c=1)<0.

EXAMPLE 7

In this example, the preparation of a catalyst is described which is obtained by the reaction of a palladium complex [PdCl(allyl)]$_2$ and the diphosphine of Example 3 having an $[\alpha_D]$=+6° (c=1, CH$_2$Cl$_2$).

1.83 mg (0.005 mmol) of palladium complex [PdCl(allyl)]$_2$ is solubilized in 0.2 ml of tetrahydrofuran, 0.01 mmol of said diphosphine in 0.3 ml of tetrahydrofuran is added and the mixture is left for 15 minutes, under agitation, at ambient temperature.

EXAMPLE 8

In this example, the preparation of a catalyst is described which is obtained by the reaction of a palladium complex [PdCl(allyl)]$_2$ and the diphosphine of Example 4: the diphosphine used having an $[\alpha_D]$=+114° (c=9.5, CH$_2$Cl$_2$).

1.83 mg (0.005 mmol) of palladium complex [PdCl(allyl)]$_2$ is solubilized in 0.2 ml of tetrahydrofuran, 0.01 mmol of said diphosphine in 0.3 ml of tetrahydrofuran is added and the mixture is left for 15 minutes, under agitation, at ambient temperature.

EXAMPLES 9 AND 10

In these examples, an allylic substitution reaction is carried out.

72 mg of sodium hydride (1.8 mmol) in 2 ml of hexane is placed in a schlenk tube under argon and the mixture is agitated for 1 minute then the hexane is removed.

4 ml of tetrahydrofuran is added to the sodium hydride followed by 0.23 ml of ethyl malonate (2 mmol) at 0° C.

An anion forms and the medium is taken to ambient temperature then 250 mg of 1,3-diphenylpropenyl acetate (1 mmol) prepared according to Bosnich et al. [J. Am. Chem. Soc. 107, 2033 (1985)] in solution in 1 ml of tetrahydrofuran and then the catalytic system are added.

The medium is heated to the reflux temperature of the solvent.

After total reaction, the reaction medium is hydrolyzed with 4 ml of acetic acid then extracted with ether.

The organic phase is washed with water, dried over anhydrous magnesium sulphate then evaporated under reduced pressure of 25 mm of mercury.

The residue is chromatographed on silica gel, with the following eluants: hexane/ethyl acetate 80/20 for the starting allyl Rf=0.4 and Rf=0.3 for the product formed.

The two catalysts of Examples 7 and 8 allow 1,3-diphenylpropenyl dimethylmalonate to be obtained, after heating for one hour with a yield and an enantiomeric excess (ee) stated in the following Table 1:

TABLE 1

| Ex. No. | Nature of catalyst | Yield (%) | Enantiomeric excess (%) |
|---------|--------------------|-----------|--------------------------|
| 9       | Example 7          | 90        | 55                       |
| 10      | Example 8          | 94        | 45                       |

EXAMPLE 11

The diphosphine of Example 1 is prepared according to the same operating method except for the fact that the meso and d/l diastereoisomers are separated according to a sulphide then oxide route.

6,6'bis-(1-phospha-3-phenyl-2,4,5-dimethylnorbornadiene) disulphide in Racemic Form (IX'r)

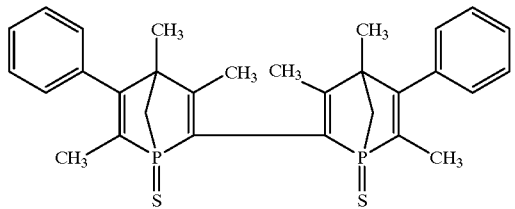

The operation starts with the preparation of 6,6'bis-(1-phospha-3-phenyl-2,4,5-dimethylnorbornadiene) in meso form (Im) and in racemic form (Ir) according to the same operating method as Example 1.

4.9 g of this mixture are solubilized in 20 ml of toluene then 1.65 g of sulphur is added.

The mixture is heated for 20 minutes at 80° C.

5.3 g of diastereoisomers are obtained which are then separated on silica gel with ethyl acetate as eluant.

The first diastereoisomer (1.75 g) corresponds to the racemic mixture (Rf=0.29 and yield=30%) and has the following NMR characteristics:

NMR $^{31}$P: δ(toluene)=51 ppm

The second diastereoisomer (3.5 g) corresponds to meso (Rf=0.17 and yield=70%) and has the following NMR characteristics:

NMR $^{31}$P: δ(ethyl acetate) δa=51.05 ppm and δb=53.75 ppm (AB, $^3$JPP=6.5 Hz).

6,6'bis-(1-phospha-3-phenyl-2,4,5-dimethylnorbornadiene) dioxide in Racemic Form (IXr)

1.25 g (2.4 mmol) of the first diastereoisomer obtained previously is solubilized, under a current of argon, in 10 ml of CH$_2$Cl$_2$, then 1.1 g of CF$_3$COOH (9.65 mmol) and 0.95 of cyclohexene oxide (9.65 mmol) are added.

The mixture is heated at reflux of the solvent for 30 minutes.

The excess acid is neutralized with a solution of sodium carbonate then the aqueous phase is extracted with ether.

The organic phases are combined and dried over anhydrous magnesium sulphate.

The solvent is evaporated off.

The residue is purified by chromatography on silca gel with an ethyl acetate/methanol mixture (90/10).

1.12 g of racemic diphosphine dioxide is obtained i.e. a yield of 95%.

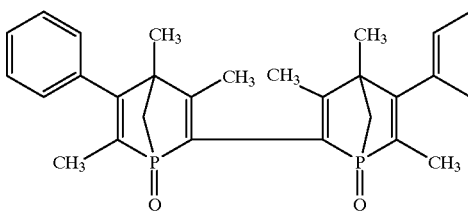

The NMR characteristics of the racemic mixture are as follows:

NMR $^{31}$P: δ(CH$_2$Cl$_2$)=53.1 ppm (IXr)

Then the two enantiomers are separated after reduction of the racemic diphosphine dioxide according to the same operating method of Example 1.

What is claimed is:

1. A 6,6'-bis-(1-phosphanorbornadiene) diphosphine dioxide corresponding to the following formula:

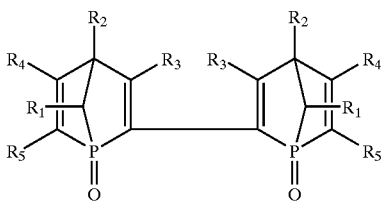

(IX)

wherein:

- R$_1$, R$_2$, R$_3$, R$_4$, R$_5$, identical or different, represent a hydrogen atom or a hydrocarbon radical optionally substituted, having from 1 to 40 carbon atoms, selected from a linear or branched, saturated or unsaturated acyclic aliphatic radical; a monocyclic or polycyclic, saturated, unsaturated or aromatic, carbocyclic or heterocyclic radical; a linear or branched, saturated or unsaturated aliphatic radical, carrying a cyclic substituent;
- R$_2$ and R$_3$ together with the carbon atoms which carry them optionally can form a saturated or unsaturated ring;

R$_5$ optionally can represent a radical of the formula

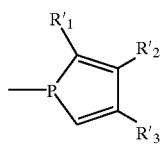

in which R$_1$', R$_2$ ', and R$_3$' have the same meaning as that given for R$_1$, R$_2$ and R$_3$; and R$_4$ and R$_5$ cannot simultaneously represent a phenyl group.

2. A 6,6'-bis-(1-phosphanorbornadiene) diphosphine dioxide according to claim 1 in optically active form corresponding to the following formulae:

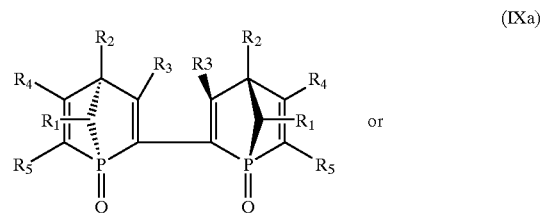

(IXa) or

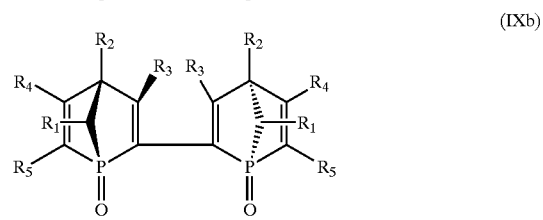

(IXb)

and in meso form:

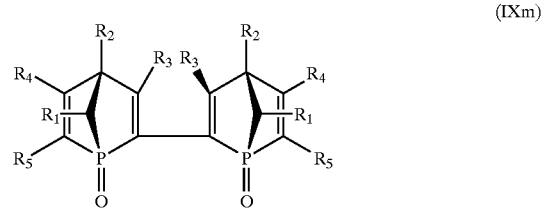

(IXm)

and in racemic form:

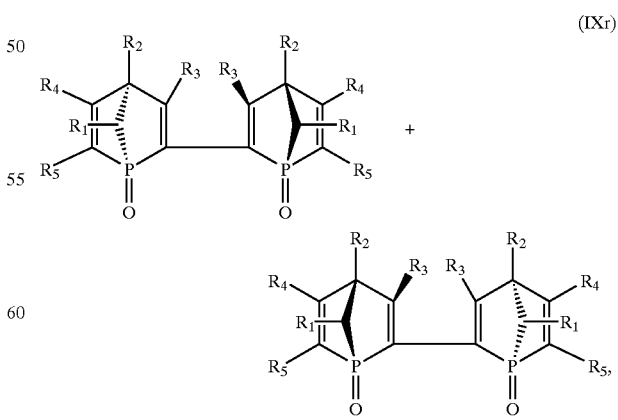

(IXr)

wherein in formulae (IXa), (IXb), IXm) and (IXr), R$_1$ to R$_5$ have the meanings given in claim 1.

3. Preparation process for a diphosphine dioxide of formula (IX) described in claim 1 which comprises oxidizing a diphosphine of formula (I) using an oxidizing agent, wherein formula (I) is as follows:

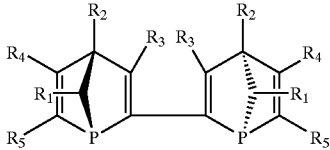
(I)

and $R_1$ to $R_5$ have the meanings given in claim 1.

4. Preparation process for a diphosphine dioxide in meso form or in racemic form described in claim 2 which comprises oxidizing a diphosphine in meso form (Im) and in racemic form (Ir), then separating the two diasteroisomers of the diphosphine dioxides, wherein formulae (Im) and (Ir) are as follows:

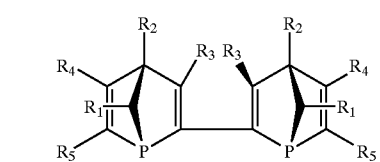
(Im)

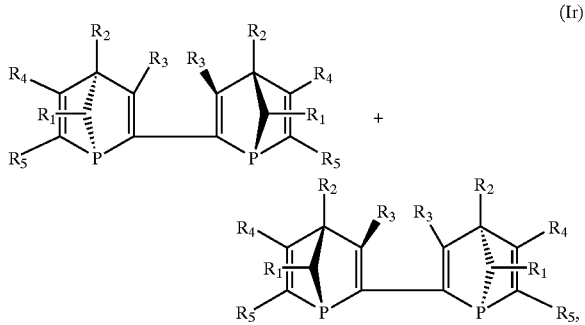
(Ir)

and $R_1$ to $R_5$ have the meanings given in claim 2.

5. Process according to claim 4 wherein the diphosphine in meso form (Im) and in racemic form (Ir) is obtained by a process comprising reacting a diphosphole of formula (III) originating from the rearrangement of a diphosphole of formula (IV):

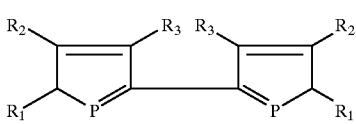
(III)

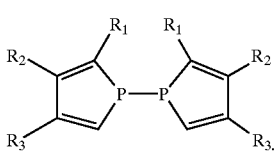
(IV)

and an acetylenic compound of formula (V):

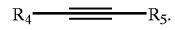
(V)

6. Process according to claim 4 wherein the oxidizing agent is a hydrogen peroxide solution.

7. Process according to claim 4, wherein the two diasteroisomers (IXm) and (IXr)

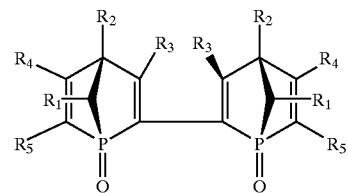
(IXm)

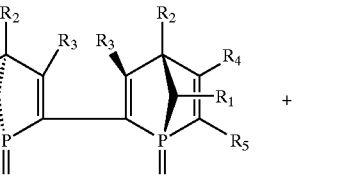
(IXr)

+

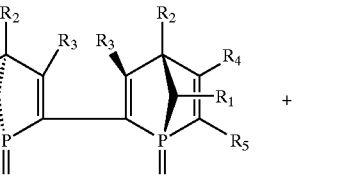

are separated by liquid column chromatography, allowing firstly the diphosphine dioxide to be obtained in meso form (IXm) and the diphosphine dioxide to be obtained in racemic form (IXr).

8. Preparation process for an optically active diphosphine of formula (Ia) or (Ib)

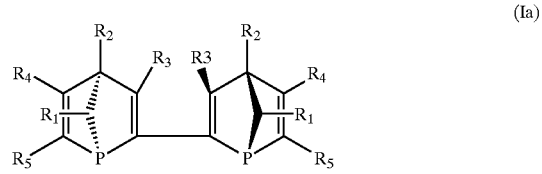
(Ia)

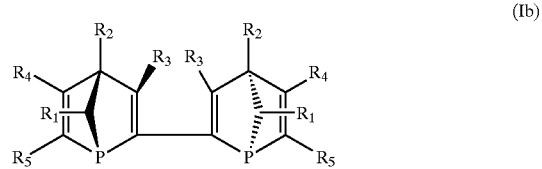
(Ib)

which comprises the steps of:

carrying out the resolution of diphosphine dioxide in racemic form (IXr),

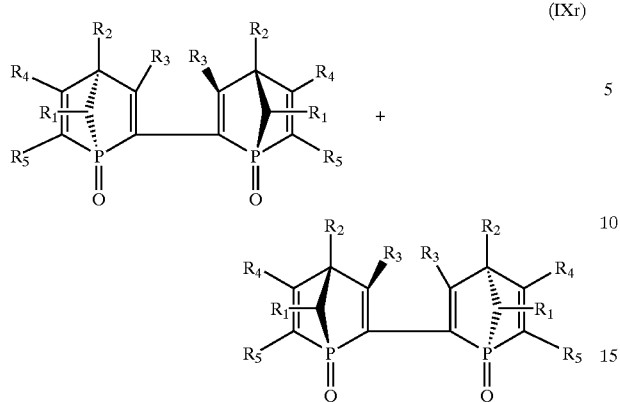

(IXr)

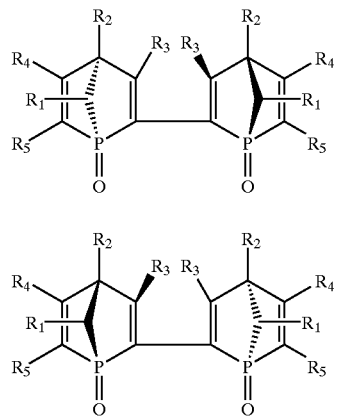

(IXa)

(IXb)

to separate enantiomers IXa and IXb then separately carrying out the reduction of the diphosphine dioxide enantiomers (IXa) or (IXb), wherein $R_1$, $R_2$, $R_3$, $R_4$, $R_5$, identical or different, represent a hydrogen atom or hydrocarbon radical optionally substituted, having from 1 to 40 carbon atoms, which can be a linear or branched, saturated or unsaturated acyclic aliphatic radical; a monocyclic or polycyclic, saturated, unsaturated or aromatic, carbocyclic or heterocyclic radical; a linear or branched, saturated or unsaturated aliphatic radical, carrying a cyclic substituent;

$R_2$ and $R_3$ together with the carbon atoms which carry them can form a saturated or unsaturated ring;

$R_5$ can represent a radical of

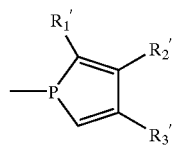

type, in which $R_1'$, $R_2'$ and $R_3'$ have the same meaning as that given for $R_1$, $R_2$ and $R_3$; and $R_4$ and $R_5$ cannot simultaneously represent a phenyl group.

9. Process according to claim 8 characterized in that the resolution of (IXr) is carried out by chiral liquid chromatography.

10. Preparation process for an optically active diphosphine of formula (Ia) or (Ib)

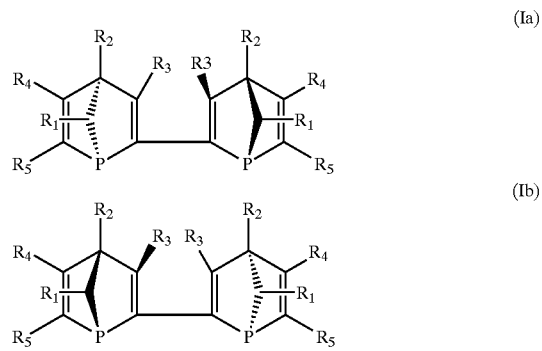

(Ia)

(Ib)

which comprises the steps of:

carrying out the reduction of diphosphine dioxide in racemic form (IXr),

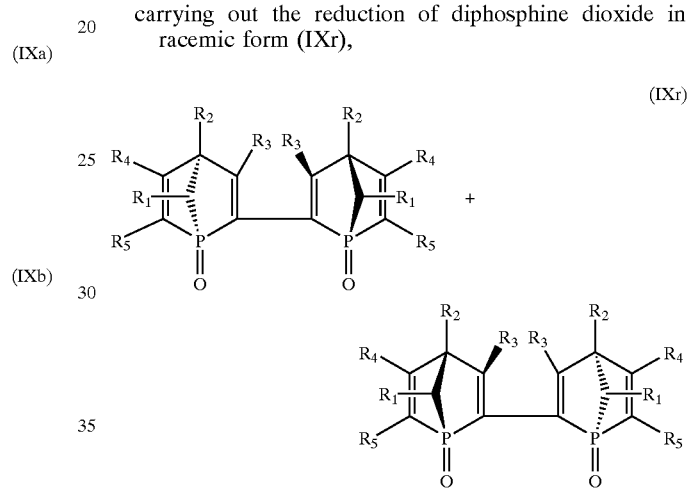

(IXr)

leading to the diphosphine in racemic form (Ir),

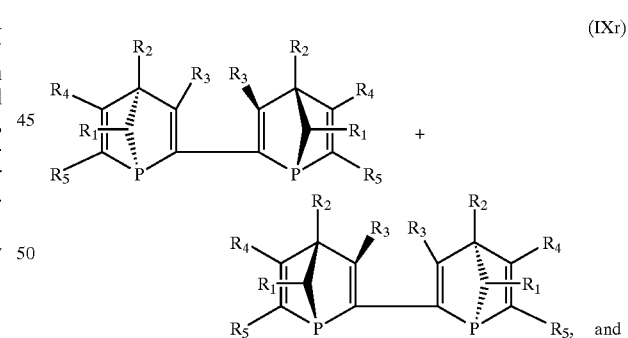

(IXr)

and carrying out the resolution of the diphosphine in racemic form (Ir), to separate the enantiomers, wherein $R_1$, $R_2$, $R_3$, $R_4$, $R_5$, identical or different, represent a hydrogen atom or hydrocarbon radical optionally substituted, having from 1 to 40 carbon atoms, which can be a linear or branched, saturated or unsaturated acyclic aliphatic radical; a monocyclic or polycyclic, saturated, unsaturated or aromatic, carbocyclic or heterocyclic radical; a linear or branched, saturated or unsaturated aliphatic radical, carrying a cyclic substituent;

$R_2$ and $R_3$ together with the carbon atoms which carry them can form a saturated or unsaturated ring;

$R_5$ can represent a radical of

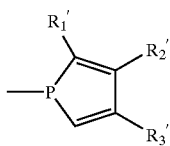

type, in which $R_1'$, $R_2'$ and $R_3'$ have the same meaning as that given for $R_1$, $R_2$ and $R_3$; and $R_4$ and $R_5$ cannot simultaneously represent a phenyl group.

11. Process according to claim 10 wherein the reduction is carried out by a reducing agent selected from the group consisting of trichlorosilane, hexachlorodisilazane, phenyltrisilane, and a hydride.

12. Process according to claim 11, wherein a base is added.

13. A process according to claim 5, wherein the diphosphole of formula (III) is obtained from a diphosphole of formula (IV) by thermal treatment carried out at a temperature between 100° C. and 200°.

14. Process according to claim 5 wherein the diphosphole of formula (IV) is 1,1'-bis-(3,4-dimethylphosphole), 1,1'-bis-(3-methylphosphole) or 1,1'-bis- (phosphole).

15. Process According to claim 5, wherein the acetylenic compound of formula (V) is acetylene, methylacetylene, tert-butylacetylene, phenylacetylene, phenylmethylacetylene, o-tolylacetylene, bis-(o-tolylacetylene), phenyl-tert-butylacetylene, phenylmesitylacetylene or bis-(mesityl)acetylene.

16. Process according to claim 12, wherein the base is a tertiary amine.

17. Process according to claim 16, wherein the tertiary amine is a picoline, pyridine, 2-ethylpyridine, 4-ethylpyridine, 2-methylpyridine, 4-methylpyridine, 2,6-dimethylpyridine, imidazole, 1-methylimidazole, TMEDA (tetramethylenediamine), N-methylpyrrolidine, 4-methylmorpholine, triethylamine or DBU (1,8-diazabicycloundecene-7).

18. Process according to claim 11, wherein the hydride is $LiAlH_4$ or $NaBH_4$.

* * * * *